(12) United States Patent
Venkataraman et al.

(10) Patent No.: US 7,412,332 B1
(45) Date of Patent: Aug. 12, 2008

(54) METHOD FOR ANALYZING POLYSACCHARIDES

(75) Inventors: Ganesh Venkataraman, Bedford, MA (US); Zachary Shriver, Boston, MA (US); Rahul Raman, Cambridge, MA (US); Ram Sasisekharan, Bedford, MA (US); Nishla Keiser, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/557,997

(22) Filed: Apr. 24, 2000

Related U.S. Application Data

(60) Provisional application No. 60/159,939, filed on Oct. 14, 1999, provisional application No. 60/159,940, filed on Oct. 14, 1999, provisional application No. 60/130,747, filed on Apr. 23, 1999, provisional application No. 60/130,792, filed on Apr. 23, 1999.

(51) Int. Cl.
*G06F 19/00* (2006.01)
(52) U.S. Cl. ............................. 702/19; 707/6; 707/102; 703/2
(58) Field of Classification Search .................. 707/6; 211/41.12; 702/19
See application file for complete search history.

(56) References Cited

U.S. PATENT DOCUMENTS

| 4,281,108 A | 7/1981 | Fussi |
| 4,303,651 A | 12/1981 | Lindahl et al. |
| 4,341,869 A | 7/1982 | Langer, Jr. et al. |
| 4,373,023 A | 2/1983 | Langer et al. |
| 4,396,762 A | 8/1983 | Langer et al. |
| 4,443,545 A | 4/1984 | Langer, Jr. et al. |
| 4,455,380 A | 6/1984 | Adachi |
| 4,486,420 A | 12/1984 | Lormeau et al. |
| 4,551,296 A | 11/1985 | Kavesh et al. |

(Continued)

FOREIGN PATENT DOCUMENTS

EP 0 140 781 A2 5/1985

(Continued)

OTHER PUBLICATIONS

Claverie et al., "Information Enhancement Methods for Large Scale Sequence Analysis", 1993, Computers and Chemistry, vol. 17, No. 2, pp. 191-201.*

(Continued)

*Primary Examiner*—Carolyn Smith
(74) *Attorney, Agent, or Firm*—Wolf, Greenfield & Sacks, P.C.

(57) ABSTRACT

A data structure, tangibly embodied in a computer-readable medium, representing a polymer of chemical units is disclosed. The data structure includes an identifier including a plurality of fields for storing values corresponding to properties of the polymer. The polymer may, for example, be a polysaccharide and the chemical units may be saccharides. Also disclosed is a computer-implemented method for determining whether properties of a query sequence of chemical units match properties of a polymer of chemical units. The query sequence is represented by a first data structure, and the polymer is represented by a second data structure, each are tangibly embodied in a computer-readable medium, including an identifier including a plurality of bit fields for storing values corresponding to properties of the query sequence and polymer, respectively. The invention also involves a notational system referred to as Property Encoded Nomenclature.

23 Claims, 5 Drawing Sheets

U.S. PATENT DOCUMENTS

| | | |
|---|---|---|
| 4,679,555 A | 7/1987 | Sackner |
| 4,692,435 A | 9/1987 | Lormeau et al. |
| 4,745,105 A | 5/1988 | Griffin et al. |
| 4,757,056 A | 7/1988 | Van Gorp et al. |
| 4,784,820 A | 11/1988 | Kavesh |
| 4,830,013 A | 5/1989 | Maxwell |
| 4,928,694 A | 5/1990 | Maxwell |
| 4,942,156 A | 7/1990 | Foley et al. |
| 4,990,502 A | 2/1991 | Lormeau et al. |
| 5,010,063 A | 4/1991 | Piani et al. |
| 5,039,529 A | 8/1991 | Bergendal et al. |
| 5,106,734 A | 4/1992 | Nielsen |
| 5,110,918 A | 5/1992 | Casu et al. |
| 5,152,784 A | 10/1992 | Tsilibary |
| 5,164,378 A | 11/1992 | Conti et al. |
| 5,169,772 A | 12/1992 | Zimmerman et al. |
| 5,204,323 A | 4/1993 | Findlay et al. |
| 5,252,339 A | 10/1993 | Cristofori et al. |
| 5,262,325 A | 11/1993 | Zimmermann et al. |
| 5,284,558 A | 2/1994 | Linhardt et al. |
| 5,290,695 A | 3/1994 | Morikawa et al. |
| 5,338,677 A | 8/1994 | Zimmermann et al. |
| 5,389,539 A | 2/1995 | Sasisekharan et al. |
| 5,389,618 A | 2/1995 | Debrie |
| 5,418,259 A | 5/1995 | Broos et al. |
| 5,453,171 A | 9/1995 | Ma et al. |
| 5,474,987 A | 12/1995 | Cohen et al. |
| 5,567,417 A | 10/1996 | Sasisekharan et al. |
| 5,569,366 A | 10/1996 | Chen et al. |
| 5,569,600 A | 10/1996 | Sasisekharan et al. |
| 5,576,304 A | 11/1996 | Kakkar et al. |
| 5,597,811 A | 1/1997 | Gruber |
| 5,599,801 A | 2/1997 | Branellec et al. |
| 5,607,859 A | 3/1997 | Biemann et al. |
| 5,618,917 A | 4/1997 | Toback et al. |
| 5,619,421 A | 4/1997 | Venkataraman et al. |
| 5,681,733 A | 10/1997 | Su et al. |
| 5,687,090 A | 11/1997 | Chen et al. |
| 5,714,376 A | 2/1998 | Sasisekharan et al. |
| 5,744,515 A | 4/1998 | Clapper |
| 5,752,019 A | 5/1998 | Rigoutsos et al. |
| 5,753,445 A | 5/1998 | Fillit et al. |
| 5,759,767 A | 6/1998 | Lakowicz et al. |
| 5,763,427 A | 6/1998 | Weitz et al. |
| 5,767,269 A | 6/1998 | Hirsh et al. |
| 5,770,420 A * | 6/1998 | Lowe et al. ............... 435/193 |
| 5,776,434 A | 7/1998 | Purewal et al. |
| 5,795,875 A | 8/1998 | Holme et al. |
| 5,808,021 A | 9/1998 | Holme et al. |
| 5,824,299 A | 10/1998 | Luster et al. |
| 5,830,726 A | 11/1998 | Sasisekharan et al. |
| 5,855,913 A | 1/1999 | Hanes et al. |
| 5,856,928 A | 1/1999 | Yan |
| 5,874,064 A | 2/1999 | Edwards et al. |
| 5,879,713 A | 3/1999 | Roth et al. |
| 5,919,693 A | 7/1999 | Su et al. |
| 5,922,358 A | 7/1999 | Doutremepuich et al. |
| 5,952,653 A | 9/1999 | Covey et al. |
| 5,968,822 A | 10/1999 | Pecker et al. |
| 5,985,309 A | 11/1999 | Edwards et al. |
| 5,990,097 A | 11/1999 | Kennedy |
| 5,993,846 A | 11/1999 | Friedman et al. |
| 5,997,863 A | 12/1999 | Zimmermann et al. |
| 6,004,771 A | 12/1999 | Thornton |
| 6,013,628 A | 1/2000 | Skubitz et al. |
| 6,116,237 A | 9/2000 | Schultz et al. |
| 6,136,295 A | 10/2000 | Edwards et al. |
| RE37,053 E | 2/2001 | Hanes et al. |
| 6,190,522 B1 | 2/2001 | Haro |
| 6,190,875 B1 | 2/2001 | Ben-Artzi et al. |
| 6,217,863 B1 | 4/2001 | Godavarti et al. |
| 6,228,654 B1 | 5/2001 | Chait et al. |
| 6,268,146 B1 | 7/2001 | Shultz et al. |
| 6,291,439 B1 | 9/2001 | Klock |
| 6,309,853 B1 | 10/2001 | Friedman et al. |
| 6,319,680 B1 | 11/2001 | Yasuno et al. |
| 6,333,051 B1 | 12/2001 | Kabanov et al. |
| 6,368,642 B2 | 4/2002 | Kreiberg et al. |
| 6,429,302 B1 | 8/2002 | Kennedy |
| 6,440,705 B1 | 8/2002 | Stanton et al. |
| 6,569,366 B1 | 5/2003 | Toyohara et al. |
| 6,597,996 B1 | 7/2003 | Venkataraman et al. |
| 6,610,484 B1 | 8/2003 | Hung |
| 6,642,363 B1 | 11/2003 | Mooney et al. |
| 6,653,076 B1 | 11/2003 | Franza et al. |
| 6,734,288 B2 * | 5/2004 | Filvaroff et al. .......... 530/387.9 |
| 6,869,789 B2 | 3/2005 | Liu et al. |
| 6,962,699 B2 | 11/2005 | Pojasek et al. |
| 7,056,504 B1 | 6/2006 | Sasisekharan et al. |
| 7,083,937 B2 | 8/2006 | Sasisekharan et al. |
| 7,105,334 B2 | 9/2006 | Pojasek et al. |
| 7,110,889 B2 | 9/2006 | Venkataraman et al. |
| 7,117,100 B2 | 10/2006 | Venkataraman et al. |
| 7,129,335 B2 | 10/2006 | Pojasek et al. |
| 7,139,666 B2 | 11/2006 | Venkataraman |
| 7,247,445 B2 | 7/2007 | Sasisekharan et al. |
| 7,270,815 B2 | 9/2007 | Sasisekharan et al. |
| 2002/0122793 A1 | 9/2002 | Liu et al. |
| 2002/0128225 A1 | 9/2002 | Liu et al. |
| 2002/0169143 A1 | 11/2002 | Sasisekharan et al. |
| 2002/0172961 A1 | 11/2002 | Schneider et al. |
| 2003/0008326 A1 | 1/2003 | Sem et al. |
| 2003/0008820 A1 | 1/2003 | Kwan et al. |
| 2003/0096281 A1 | 5/2003 | Venkataraman et al. |
| 2003/0099628 A1 | 5/2003 | Liu et al. |
| 2003/0191587 A1 | 10/2003 | Venkataraman et al. |
| 2003/0203385 A1 | 10/2003 | Venkataraman et al. |
| 2003/0219830 A1 | 11/2003 | Venkataraman et al. |
| 2004/0087543 A1 | 5/2004 | Shriver et al. |
| 2004/0091471 A1 | 5/2004 | Myette et al. |
| 2004/0091472 A1 | 5/2004 | Pojasek et al. |
| 2004/0092037 A1 | 5/2004 | Sasisekharan et al. |
| 2004/0147033 A1 | 7/2004 | Shriver et al. |
| 2004/0197933 A1 | 10/2004 | Venkataraman et al. |
| 2004/0204869 A1 | 10/2004 | Venkataraman et al. |
| 2004/0214228 A9 | 10/2004 | Venkataraman et al. |
| 2005/0037376 A1 | 2/2005 | Sasisekharan et al. |
| 2005/0065738 A1 | 3/2005 | Raguram |
| 2005/0214276 A9 | 9/2005 | Myette et al. |
| 2005/0227320 A1 | 10/2005 | Pojasek et al. |
| 2005/0233401 A1 | 10/2005 | Liu et al. |
| 2005/0233402 A1 | 10/2005 | Liu et al. |
| 2005/0233419 A1 | 10/2005 | Pojasek et al. |
| 2005/0266067 A1 | 12/2005 | Sengupta et al. |
| 2006/0024664 A1 | 2/2006 | Sasisekharan et al. |
| 2006/0057638 A1 | 3/2006 | Bosques et al. |
| 2006/0067927 A1 | 3/2006 | Chandrasekaran et al. |
| 2006/0067928 A1 | 3/2006 | Liu et al. |
| 2006/0078959 A1 | 4/2006 | Prabhakar et al. |
| 2006/0083711 A1 | 4/2006 | Berry et al. |
| 2006/0105430 A1 | 5/2006 | Sasisekharan et al. |
| 2006/0127950 A1 | 6/2006 | Bosques et al. |
| 2006/0154894 A1 | 7/2006 | Berry et al. |
| 2006/0177885 A1 | 8/2006 | Myette et al. |
| 2006/0177910 A1 | 8/2006 | Myette et al. |
| 2006/0177911 A1 | 8/2006 | Myette et al. |
| 2006/0182734 A1 | 8/2006 | Liu et al. |
| 2006/0183713 A1 | 8/2006 | Liu et al. |
| 2006/0183891 A1 | 8/2006 | Myette et al. |
| 2006/0292130 A1 | 12/2006 | Sasisekharan et al. |
| 2006/0292655 A1 | 12/2006 | Sasisekharan et al. |
| 2006/0292673 A1 | 12/2006 | Sasisekharan et al. |
| 2007/0004012 A1 | 1/2007 | Sasisekharan et al. |
| 2007/0020243 A1 | 1/2007 | Sengupta et al. |

| | | | |
|---|---|---|---|
| 2007/0065424 | A1 | 3/2007 | Pojasek et al. |
| 2007/0065921 | A1 | 3/2007 | Sasisekharan et al. |
| 2007/0066769 | A1 | 3/2007 | Venkataraman et al. |
| 2007/0148157 | A1 | 6/2007 | Prabhakar et al. |
| 2007/0148158 | A1 | 6/2007 | Sasisekharan et al. |
| 2007/0148740 | A1 | 6/2007 | Prabhakar et al. |
| 2007/0161073 | A1 | 7/2007 | Sasisekharan et al. |
| 2007/0202563 | A1 | 8/2007 | Prabhakar et al. |
| 2007/0224670 | A1 | 9/2007 | Prabhakar et al. |

FOREIGN PATENT DOCUMENTS

| | | |
|---|---|---|
| EP | 0 114 589 B1 | 9/1987 |
| EP | 0 244 236 A2 | 11/1987 |
| EP | 0 394 971 A1 | 10/1990 |
| EP | 0 433 225 A1 | 6/1991 |
| EP | 0 342 215 B1 | 8/1993 |
| EP | 0 557 887 A2 | 9/1993 |
| EP | 0 747 705 A1 | 12/1996 |
| FR | 2554348 | 5/1985 |
| WO | WO 92/01003 A1 | 1/1992 |
| WO | WO 93/05167 A1 | 3/1993 |
| WO | WO 93/08289 | 4/1993 |
| WO | WO 93/10450 A1 | 5/1993 |
| WO | WO 93/15406 A1 | 8/1993 |
| WO | WO 93/19096 | 9/1993 |
| WO | WO 93/19734 A1 | 10/1993 |
| WO | WO 94/12618 A1 | 6/1994 |
| WO | WO 94/21689 | 9/1994 |
| WO | WO 95/13830 A1 | 5/1995 |
| WO | WO 95/34635 | 12/1995 |
| WO | WO 96/01648 A1 | 1/1996 |
| WO | WO 96/13606 | 5/1996 |
| WO | WO 96/28169 A1 | 9/1996 |
| WO | PCT/US96/17310 | 10/1996 |
| WO | WO 96/32149 A1 | 10/1996 |
| WO | WO 97/06783 A1 | 2/1997 |
| WO | WO 97/11684 A1 | 4/1997 |
| WO | WO 97/16556 | 5/1997 |
| WO | WO 97/35562 A1 | 10/1997 |
| WO | WO 98/04902 A1 | 2/1998 |
| WO | WO 98/31346 A1 | 7/1998 |
| WO | WO 99/28462 A2 | 6/1999 |
| WO | PCT/US99/19841 | 1/2000 |
| WO | WO 00/12726 A2 | 3/2000 |
| WO | 00/65521 | 11/2000 |
| WO | WO 00/65521 A2 | 11/2000 |
| WO | WO 01/66772 | 9/2001 |
| WO | WO 02/23190 | 3/2002 |
| WO | WO 02/32406 | 4/2002 |
| WO | WO 02/077199 | 10/2002 |
| WO | WO 2003/102160 | 12/2003 |
| WO | WO 2004/055491 | 7/2004 |
| WO | WO 2004/062592 | 7/2004 |
| WO | WO 2004/069152 | 8/2004 |
| WO | WO 2005/087920 | 9/2005 |
| WO | WO 2005/110438 | 11/2005 |
| WO | WO 2005/111627 | 11/2005 |
| WO | WO 2006/076627 | 7/2006 |
| WO | WO 2006/083328 | 8/2006 |
| WO | WO 2006/088491 | 8/2006 |
| WO | WO 2006/089206 A2 | 8/2006 |
| WO | WO 2006/105313 A2 | 10/2006 |
| WO | WO 2006/105315 A2 | 10/2006 |
| WO | WO 2007/044471 A2 | 4/2007 |
| WO | WO 2007/120478 A2 | 10/2007 |

OTHER PUBLICATIONS

"antigen" definition, Merriam-Webster online dictionary, 2005, on the world wide web at http://www.m-w.com/cgi-bin/dictionary?book=Dictionary&va=antigen, 2 pages.*

"carbohydrate" definition, Merriam-Webster online dictionary, 2005, on the world wide web at http://www.m-w.com/cgi-bin/dictionary?book=Dictionary&va=carbohydrate, 2 pages.*

"saccharide" definition, Merriam-Webster online dictionary, 2005 on the world wide web at http://www.m-w.com/cgi-bin/dictionary?book=Dictionary&va=saccharide, 1 page.* van Kuik et al., "A 1H NMR database computer program for the analysis of the primary structure of complex carbohydrates", 1992, Carbohydrate Research, vol. 235, pp. 53-68.* van Kuik et al., "Databases of complex carbohydrates", 1992, Trends in Biotechnology, vol. 10, pp. 182-185.*

Doubet et al., "The Complex Carbohydrate Structure Database", 1989, Trends In Biochemical Sciences, vol. 14, pp. 475-477.*

Bohne et al., "W3-Sweet: Carbohydrate Modeling By Internet", 1998, Journal of Molecular Modeling, vol. 4, pp. 33-43.*

Hook et al., "Distribution of Sulphate and Iduronic Acid Residues in Heparin and Heparan Sulphate", 1974, Biochem. Journal, vol. 137, pp. 33-43.*

Biemann K, Four decades of structure determination by mass spectrometry: from alkaloids to heparin. *J Am Soc Mass Spectrom* 2002; 13(11):1254-1272.

Rhomberg A et al., Mass spectrometric sequencing of heparin and heparan sulfate using partial digestion with heparinases. Proc. 45th ASMS Annual Conference on Mass Spectrometry Allied Topics, Jun. 1-5, 1997, Palm Springs, CA, p. 1026-1027.

Rhomberg AJ, Mass spectrometric and capillary electrophoretic investigation of heparin, heparinases and related compounds. Ph.D. thesis, MIT (Department of Chemistry), May 22, 1998.

Venkataraman G et al., Sequencing complex polysaccharides. *Science* Oct. 15, 1999; 286:537-542.

Ameer et al., "A New Approach to Regional Heparinization: Design and Development of a Novel Immobilized Heparinase Device", *Blood Purification Meeting Information: The International Conference on Continuous Renal Replacement Therapies*, 1998, 107-108, 16(2). Abstract Only.

Berry et al., "Distinct Heparan Sulfate Glycosaminoglycans are Responsible for Mediating Fibroblast Growth Factor-2 Biological Activity Through Different Fibroblast Growth Factor Receptors", *The FASEB Journal Online*, 2001, 1-19, Article #: 10.1096/fj.00-0661fje.

Carlson et al., "Behavior of Antithrombin III Isoforms on Immobilized Heparins", *The Journal of Biological Chemistry*, 1988, 2187-2194, 263(5).

Claverie et al., "Information Enhancement Methods for Large Scale Sequence Analysis", *Computers Chem.*, 1993, 191-201, 17(2).

Crum et al., "A New Class of Steroids Inhibits Angiogenesis in the Presence of Heparin or a Heparin Fragment", *Science*, 1985, 1375-1378, 230.

Dull et al., "Lung Endothelial Heparan Sulfates Mediate Cationic Peptide-induced Barrier Dysfunction: a New Role for the Glycocalyx", *Am J Physiol Lung Cell Mol Physiol*, 2003, L986-L995, 285.

Edwards et al., "Large Porous Particles for Pulmonary Drug Delivery", *Science Reprint Series*, 1997, 1868-1871, 276.

Edwards et al., "Recent Advances in Pulmonary Drug Delivery Using Large, Porous Inhaled Particles", *J. Appl. Physoil.*, 1998, 379-385, 85(2).

Ernst et al., "Expression in *Escherichia coli*, Purification and Characterization of Heparinase I from *Flavobacterium heparinum*", *Biochem. J.*, 1996, 589-597, 315.

Ernst et al., "Enzymatic Degradation of Glycosaminoglycans", *Critical Reviews in Biochemistry and Molecular Biology*, 1995, 387-444, 30(5).

Folkman et al., "Angiogenesis Inhibition and Tumor Regression Caused by Heparin or a Heparin Fragment in the Presence of Cortisone", *Science*, 1983, 719-725, 221.

Gioldassi et al., "Determination of Phosphorylated and Sulfated Linkage-Region Oligosaccharides in Chondroitin/ Dermatan and Heparan Sulfate Proteoglycans by High Performance Liquid Chromatography", *J. Liq. Chrom. & Rel. Technol.*, 1999, 1997-2007, 22(13).

Godavarti et al., "Heparinase III from *Flavobacterium heparinum*: Cloning and Recombinant Expression in *Escherichia coli*", *Biochemical and Biophysical Research Communications*, 1996, 751-758, 225(3).

Godavarti et al., "A Comparative Analysis of the Primary Sequences and Characteristics of Heparinases I, II, and III from *Flavobacterium heparinum*", *Biochemical and Biophysical Research Communications*, 1996, 770-777, 229(3).

Godavarti et al., "Heparinase I from *Flavobacterium heparinum*", *The Journal of Biological Chemistry*, 1998, 248-255, 273(1).

Guerrini et al., "A Novel Computational Approach to Integrate NMR Spectroscopy and Capillary Electrophoresis for Structure Assignment of Heparin and Haparan Sulfate Oligosaccharides", *Glycobiology*, 2002, 713-719, 12(11).

Harenberg et al., "Anticoagulant Effects and Tissue Factor Pathway Inhibitor after Intrapulmonary Low-Molecular-Weight Heparin", *Blood Coagulance and Fibrinolysis*, 1996, 477-483, 7.

Horner, "Heterogeneity of Rat Skin Heparin Chains with High Affinity for Antithrombin", *Biochem. J.*, 1987, 693-698, 244.

Johnson et al., "Endothelial Cells Preparing to Die by Apoptosis Initiate a Program of Transcriptome and Glycome Regulation", *The FASEB Journal*, 2004, 188-190, 18.

Kanabrocki et al., "Heparin as a Therapy for Atherosclerosis: Preliminary Observations on the Intrapulmonary Administration of Low-Dose Heparin in the Morning Versus Evening Gauged by Its Effect on Blood Variables", *Chronobiology International*, 1991, 210-233, 8(3).

Kanabrocki et al., "A Quest for the Relief of Atherosclerosis: Potential Role of Intrapulmonary Heparin—A Hypothesis", *Quarterly Journal of Medicine, New Series*, 1992, 259-282, 83(300).

Keiser et al., "Direct Isolation and Sequencing of Specific Protein-Binding Glycosaminoglycans", *Nature Medicine*, 2001, 123-128, 7(1).

Kishibe et al., "Structural Requirements of Heparan Sulfate for the Binding to the Tumor-derived Adhesion Factor/ Angiomodulin That Induces Cord-like Structures to ECV-304 Human Carcinoma Cells", *The Journal of Biological Chemistry*, 2000, 15321-15329, 275(20).

Krietz et al., "Controlled Delivery of Therapeutics from Microporous Membranes. II. In vitro Degradation and Release of Heparin-loaded Poly (D,L-lactide-*co*-glycolide)", *Biomatierials*, 1997, 1645-1651, 18(24).

Liu, Dongfang, et al., "The Calcium-binding Sites of Heparinase I from *Flavobacterium heparinum* are Essential for Enzymatic Activity", *The Journal of Biological Chemistry*, 1999, 4089-4095, 274(7).

Liu, Dongfang, et al., "Dynamic Regulation of Tumor Growth and Metastasis by Heparan Sulfate Glycosaminoglycans", *Seminars in Thrombosis and Hemostasis*, 2002, 67-78, 28(1).

Liu, Dongfang, et al., "Tumor Cell Surface Heparan Sulfate as Cryptic Promotors or Inhibitors of Tumor Growth and Metastasis", *PNAS*, 2002, 568-573, 99(2).

Liu, Jian, et al., "Strategy for the Sequence Analysis of Heparin", *Glycobiology*, 1995, 765-774, 5(8).

Liu, Jian, et al., "Characterization of a Heparan Sulfate Octasaccharide That Binds to Herpes Simplex Virus Type 1 Glycoprotein D", *The Journal of Biological Chemistry*, 2002, 33456-33467, 277(36).

Liu, Jian, et al., "Heparan Sulfate D-Glucosaminyl 3-*O*-Sulfotransferase -3A Sulfates *N*-Unsubstituted Glucosamine Residues", *The Journal of Biological Chemistry*, 1999, 38155-38162, 274(53).

Marciniak, "Differential Role of Fractionated Heparin in Antithrombin-III Proteolysis", *Blood*, 1982, 576-581, 59(3).

McLean et al., "Enzymic Removal of 2-*O*-Sulphato-$\Delta_{4,5}$-Glycuronic Acid Residues From Heparin Oligosaccharides", *Proc. of the 7th Intl. Symposium of Glycoconjugates*, 1983, 68-69.

Murphy et al., "Basic Fibroblast Growth Factor Binding and Processing by Human Glioma Cells", *Molecular and Cellular Endocrinology*, 1995, 193-203, 114.

Myette et al., "The Heparin / Heparan Sulfate 2-*O*-Sulfatase from *Flavobacterium heparinum*", *The Journal of Biological Chemistry*, 2003, 12157-12166, 278(14).

Myette et al., "Molecular Cloning of the Heparin / Heparan Sulfate $\Delta 4,5$ Unsaturated Glycuronidase from *Flavobacterium heparinum*, its Recombinant Expression in *Escherichia coli*, and Biochemical Determination of its Unique Substrate Specificity", *Biochemistry*, 2002, 7424-7434, 41(23).

Myette et al., "Expression in *Escherichia coli*, Purifications and Kinetic Characterization of Human Heparan Sulfate 3-*O*-Sulfotransferase-1", *Biochemical and Biophysical Research Communications*, 2002, 1206-1213, 290(4).

Natke et al., "Heparinase Treatment of Bovine Smooth Muscle Cells Inhibits Fibroblast Growth Factor-2 Binding to Fibroblast Growth Factor Receptor but Not FGF-2 Mediated Cellular Proliferation", *Angiogenesis*, 1999, 249-257, 3.

Nesheim et al., "Dependence of Antithrombin III and Thrombin Binding Stoichiometries and Catalytic Activity on the Molecular Weight of Affinity-purified Heparin", *The Journal of Biological Chemistry*, 1986, 3214-3221, 261(7).

Padera et al., "FGF-2/ Fibroblast Growth Factor Receptor/ Heparin-like Glycosaminoglycan Interactions: a Compensation Model for FGF-2 Signaling", *The FASEB Journal*, 1999, 1677-1687, 13(13).

Pixley et al., "Preparation of Highly Stable Antithrombin-sepharose and Utilization for the Fractionation of Heparin", *Thrombosis Research*, 1982, 129-133, 26(2).

Pojasek et al., "Histidine 295 and Histidine 510 are Crucial for the Enzymatic Degradation of Heparan Sulfate by Heparinase III", *Biochemistry*, 2000, 4012-1019, 39(14).

Pojasek et al., "Biochemical Characterization of the Chondroitinase B Active Site", *The Journal of Biological Chemistry*, 2002, 31179-31186, 277(34).

Pojasek et al., "Recombinant Expression, Purification, and Kinetic Characterization of Chondroitinase AC and Chondroitinase B from *Flavobacterium heparinum*", *Biochemical and Biophysical Research Communications*, 2001, 343-351, 286(2).

Raman et al., "Identification of Structural Motifs and Amino Acids within the Structure of Human Heparan Sulfate 3-*O*-Sulfotransferase that Mediate Enzymatic Function", *Biochemical and Biophysical Research Communications*, 2002, 1214-1219, 290(4).

Raman et al., "The Heparin / Heparan Sulfate 2-*O*-Sulfatase from *Flavobacterium heparinum*", 2003, 12167-12174, 278(14), J. Biolog. Chem.

Rhomberg et al., "Mass Spectrometric and Capillary Electrophoretic Investigations of the Enzymatic Degradation of Heparin-like Glycosaminoglycans", *Proc. Natl. Acad. Sci. USA*, 1998, 4176-4181, 95.

Rhomberg et al., "Mass Spectrometric Evidence for the Enzymatic Mechanism of the Depolymerization of Heparin-like Glycosaminoglycans by Heparinase II", *Proc. Natl. Acad. Sci. USA*, 1998, 12232-12237, 95.

Sasisekharan et al., "Roles of Heparan-sulfate Glycosaminoglycans in Cancer", *Nature Reviews*, 2002, 521-528, 2.

Sasisekharan et al., "Heparin and Heparan Sulfate: Biosynthesis, Structure and Function", *Current Opinions in Biological Chemistry*, 2000, 626-631, 4(6).

Shriver et al., "Biochemical Investigations and Mapping of the Calcium-binding Sites of Heparinase 1 from *Flavobacterium heparinum*", *The Journal of Biological Chemistry*, 1999, 4082-4088, 274(7).

Shriver et al., "Sequencing of 3-O Sulfate Containing Heparin Decasaccharides with a Partial Antithrombin III Binding Site", *PNAS*, 2000, 10359-10364, 97(19).

Shriver et al., "Cleavage of the Antithrombin III Binding Site in Heparin by Heparinases and its Implication in the Generation of Low Molecular Weight Heparin", *PNAS*, 2000, 10365-10370, 97(19).

Shriver et al., "Emerging Views of Heparan Sulfate Glycosaminoglycan Structure / Activity Relationships Modulating Dynamic Biological Functions", *TCM*, 2002, 71-77, 12(2).

Sundaram et al., "Rational Design of Low-Molecular Weight Haparins with Improved In vivo Activity", *PNAS*, 2003, 651-656, 100(2).

Taylor et al., "Protamine is an Inhibitor of Angiogenesis", *Nature*, 1982, 307-312, 297.

Wishart et al., "A Single Mutuation Converts a Novel Phosphotyrosinc Binding Domain into a Dual-specificity Phosphatase", *The Journal of Biological Chemistry*, 1995, 26782-26785, 270(45).

Witkowski et al., "Conversion of a β-Ketoacyl Synthase to a Malonyl Decarboxylase by Replacement of the Active-Site Cysteine with Glutamine", *Biochemistry*, 1999, 11643-11650, 38(36).

Yamada et al., "Structural Studies on the Bacterial Lyase-resistant Tetrasaccharides Derived from the Antithrombin III-binding Site of Porcine Intestinal Heparin", *The Journal of Biological Chemistry*, 1993, 4780-4787, 268(7).

Zhang et al., "6-O-Sulfotransferase-1 Represents a Critical Enzyme in the Anticoagulant Heparan Sulfate Biosynthetic Pathway", *The Journal of Biological Chemistry*, 2001, 42311-42321, 276(45).

[No Author Listed] Aqua Peptides. Online at http://www.sigmaaldrich.com. Printed Jul. 8, 2005, 3pp.

[No Author Listed] MIT News Office. "MIT Tool Impacts Multi-Billion Dollar Drug." Online at http://www.sciencedaily.com. Printed Sep. 21, 2000, 3pp.

Achur et al., Characterization of proteoglycans of human placenta and identification of unique chondroitin sulfate proteoglycans of the intervillous spaces that mediate the adherence of *Plasmodium falciparum*-infected erythrocytes to the placenta. J Biol Chem. Dec. 22, 2000;275(51):40344-56.

Anumula et al., High-sensitivity and high-resolution methods for glycoprotein analysis. Anal Biochem. Jul. 15, 2000;283(1):17-26.

Behr et al., Quantification of isomers from a mixture of twelve heparin and heparan sulfate disaccharides using tandem mass spectrometry. Rapid Commun Mass Spectrom. 2005;19(18):2553-62.

Belanger et al., Molecular mass and carbohydrate structure of prostate specific antigen: studies for establishment of an international PSA standard. Prostate. Oct. 1995;27(4):187-97.

Bengtsson et al., Interaction of lipoprotein lipase with native and modified heparin-like polysaccharides. Biochem J. Sep. 1, 1980;189(3):625-33.

Berry et al., Distinct heparan sulfate glycosaminoglycans are responsible for mediating fibroblast growth factor-2 biological activity through different fibroblast growth factor receptors. FASEB J. Jun. 2001;15(8):1422-4.

Berry et al., Distinct heparan sulfate glycosaminoglycans are responsible for mediating fibroblast growth factor-2 biological activity through different fibroblast growth factor receptors. FASEB Journal express article 10.1096/fj.00-0661fje. Published onlien Apr. 6, 2001. 19 pages.

Bourin et al., Glycosaminoglycans and the regulation of blood coagulation. Biochem J. .Jan. 15, 1993;289( Pt 2):313-30.

Brockhausen et al., Pathways of O-glycan biosynthesis in cancer cells. Biochim Biophys Acta. Dec. 6, 1999;1473(1):67-95.

Callas et al., Comparative pharmacologic profile of a glycosaminoglycan mixture, Sulodexide, and a chemically modified heparin derivative, Suleparoide. Semin Thromb Hemost. 1993; 19 Suppl 1:49-57.

Casu et al., Structural characterization of low molecular weight heparins. Semin Thromb Hemost. 1999;25 Suppl 3:17-25.

Casu et al., Characterization of sulfation patterns of beef and pig mucosal heparins by nuclear magnetic resonance spectroscopy. Arzneimittelforschung. May 1996;46(5):472-7.

Cointe et al., Unusual N-glycosylation of a recombinant human erythropoietin expressed in a human lymphoblastoid cell line does not alter its biological properties. Glycobiology. May 2000;10(5):511-9.

Conrad et al., Structure of heparan sulfate and dermatan sulfate. Ann N Y Acad Sci. 1989;556:18-28.

Dai et al., HSulf-1 and HSulf-2 are potent inhibitors of myeloma tumor growth in vivo. J Biol Chem. Dec. 2, 2005;280(48):40066-73.

Desai et al., Molecular weight of low molecular weight heparins by 13C nuclear magnetic resonance spectroscopy. Carbohydr Res. Mar. 4, 1994;255:193-212.

Desai et al., Specificity studies on the heparin lyases from *Flavobacterium heparinum*. Biochemistry. Aug. 17, 1993;32(32):8140-5.

Dietrich et al., Enzymic degradation of heparin. A glucosaminidase and a glycuronidase from *Flavobacterium heparinum*. Biochemistry. May 1969;8(5):2089-94.

Dietrich et al., Sequential degradation of heparin in *Flavobacterium heparinum*. Purification and properties of five enzymes involved in heparin degradation. J Biol Chem. Sep. 25, 1973;248(18):6408-15.

Dull et al., Lung endothelial heparan sulfates mediate cationic peptide-induced barrier dysfunction: a new role for the glycocalyx. Am J Physiol Lung Cell Mol Physiol. Nov. 2003;285(5):L986-95.

Duteil et al., Identification of heparin oligosaccharides by direct coupling of capillary electrophoresis/ionspray-mass spectrometry. Rapid Commun Mass Spectrom. 1999;13(19):1889-98.

Ernst et al., Enzymatic degradation of glycosaminoglycans. Crit Rev Biochem Mol Biol. 1995;30(5):387-444.

Forno et al., N- and O-linked carbohydrates and glycosylation site occupancy in recombinant human granulocyte-macrophage colony-stimulating factor secreted by a Chinese hamster ovary cell line. Eur J Biochem. Mar. 2004;271(5):907-19.

Gacesa et al., Enzymic degradation of alginates. Int J Biochem. Apr. 1992;24(4):545-52.

Gandra et al., Anticoagulant sulfated glycosaminoglycans in the tissues of the primitive chordate *Styela plicata* (Tunicata). Glycobiology. Dec. 2000;10(12):1333-40.

Gaucher et al., STAT: a saccharide topology analysis tool used in combination with tandem mass spectrometry. Anal Chem. Jun. 1, 2000;72(11):2331-6.

Gu et al., Purification, characterization and specificity of chondroitin lyases and glycuronidase from *Flavobacterium heparinum*. Biochem J. Dec. 1, 1995;312 ( Pt 2):569-77.

Habuchi et al., Diversity and functions of glycosaminoglycan sulfotransferases. Biochim Biophys Acta. Apr. 6, 2000;1474(2):115-27.

Harvey et al., Identification of protein-bound carbohydrates by mass spectrometry. Proteomics. Feb. 2001;1(2):311-28.

Hashimoto et al., Unsaturated glucuronyl hydrolase of *Bacillus* sp. GL1: novel enzyme prerequisite for metabolism of unsaturated oligosaccharides produced by polysaccharide lyases. Arch Biochem Biophys. Aug. 15,1999;368(2):367-74.

Hovingh et al., Specificity of flavobacterial glycuronidases acting on disaccharides derived from glycosaminoglycans. Biochem J. Aug. 1, 1977;165(2):287-93.

Hricovini et al., Structure of heparin-derived tetrasaccharide complexed to the plasma protein antithrombin derived from NOEs, J-couplings and chemical shifts. Eur J Biochem. May 1999;261(3):789-801.

Huang et al., Low-molecular-weight heparins. Hematol Oncol Clin North Am. Dec. 1998;12(6):1251-81, vi-vii.

Huige et al., Force field parameters for sulfates and sulfamates bases on Ab Initio calculations: Extensions of Amber and Charmm fields. J Comp Chem. 1995;16(1):56-79.

Hulett et al., Cloning of mammalian heparanase, an important enzyme in tumor invasion and metastasis. Nat Med. Jul. 1999;5(7):803-9.

Johannes et al., Sugars related to heparin inhibit tumors: Study of mice suggests the anticlotting drug may be used for cancer. Wall Street Journal. Jan. 22, 2002. B3.

Jones et al., Octamer sequencing technology: Optimization using fluorescent chemistry. ABRF News. 1998;9(2):1-24.

Kaji et al., Lectin affinity capture, isotope-coded tagging and mass spectrometry to identify N-linked glycoproteins. Nat Biotechnol. Jun. 2003;21(6):667-72. Abstract Only.

Kakehi et al., Analysis of glycoproteins, glycopeptides and glycoprotein-derived oligosaccharides by high-performance capillary electrophoresis. J Chromatogr A. Jan. 12, 1996;720(1-2):377-93.

Kjellen et al., Proteoglycans: structures and interactions. Annu Rev Biochem. 1991;60:443-75.

Küster et al., 18O-labeling of N-glycosylation sites to improve the identification of gel-separated glycoproteins using peptide mass mapping and database searching. Anal Chem. Apr. 1, 1999;71(7):1431-40.

Landberg et al., Carbohydrate composition of serum transferrin isoforms from patients with high alcohol consumption. Biochem Biophys Res Commun. May 16, 1995;210(2):267-74.

Landberg et al., Changes in glycosylation of human bile-salt-stimulated lipase during lactation. Arch Biochem Biophys. May 15, 2000;377(2):246-54.

Lapadula et al., Congruent strategies for carbohydrate sequencing. 3. OSCAR: an algorithm for assigning oligosaccharide topology from MS(n) data. Anal Chem. Oct. 1, 2005;77(19):6271-9.

Lind et al., Biosynthesis of heparin/heparan sulfate. Identification of a 70-kDa protein catalyzing both the D-glucuronosyl- and the N-acetyl-D-glucosaminyltransferase reactions. J Biol Chem. Oct. 5, 1993;268(28):20705-8.

Lindahl et al., Common binding sites for beta-amyloid fibrils and fibroblast growth factor-2 in heparan sulfate from human cerebral cortex. J Biol Chem. Oct. 22, 1999;274(43):30631-5.

Lopez et al., Microheterogeneity of the oligosaccharides carried by the recombinant bovine lactoferrin expressed in *Mamestra brassicae* cells. Glycobiology. Jul. 1997;7(5):635-51.

Lyon et al., Bio-specific sequences and domains in heparan sulphate and the regulation of cell growth and adhesion. Matrix Biol. Nov. 1998;17(7):485-93.

Ma et al., Carbohydrate analysis of a chimeric recombinant monoclonal antibody by capillary electrophoresis with laser-induced fluorescence detection. Anal Chem. Nov. 15, 1999;71(22):5185-92.

Maimone et al., Structure of a dermatan sulfate hexasaccharide that binds to heparin cofactor II with high affinity. J Biol Chem. Oct. 25, 1990;265(30):18263-71. Erratum in: J Biol Chem Aug. 5, 1991;266(22):14830.

Manzi et al., Exploring the glycan repertoire of genetically modified mice by isolation and profiling of the major glycan classes and nano-NMR analysis of glycan mixtures. Glycobiology. Jul. 2000;10(7):669-89.

Marciniak., Differential role of fractionated heparin in antithrombin-III proteolysis. Blood. Mar. 1982;59(3):576-81.

Mascellani et al., Structure and contribution to the heparin cofactor II-mediated inhibition of thrombin of naturally oversulphated sequences of dermatan sulphate. Biochem J. Dec. 15, 1993;296 ( Pt 3):639-48.

McLean et al., Action of heparinase II on pig mucosal heparin. Proc. Of the 8$^{th}$ International Symposium on Glycoconjugates. 1985. Abstract 73-74.

McLean et al., *Flavobacterium heparinum* 2-O-sulphatase for 2-O-sulphato-delta 4,5-glycuronate-terminated oligosaccharides from heparin. Eur J Biochem. Dec. 17, 1984;145(3):607-15.

Mechref et al., Structural investigations of glycoconjugates at high sensitivity. Chem Rev. Feb. 2002;102(2):321-69.

Mechref et al., Matrix-assisted laser desorption/ionization mass spectrometry of acidic glyconjugates facilitated by the use of spermine as a co-matrix. J Am Soc Mass Spectrom. 1998;9:1293-302.

Merry et al., Highly sensitive sequencing of the sulfated domains of heparan sulfate. J Biol Chem. Jun. 25, 1999;274(26):18455-62.

Morelle et al., Glycomics and mass spectrometry. Curr Pharm Des. 2005;11(20):2615-45. Abstract Only.

Morgenstern et al., Chondroitin sulphate proteoglycans in the CNS injury response. Prog Brain Res. 2002;137:313-32. Abstract Only.

Mulloy et al., Assignment of the 1H-n.m.r. spectra of heparin and heparan sulphate. Carbohydr Res. Dec. 15, 1987;170(2):151-65. Abstract Only.

Nadanaka et al., The unusual tetrasaccharide sequence GlcA beta 1-3GalNAc(4-sulfate)beta 1-4GlcA(2-sulfate)beta 1-3GalNAc(6-sulfate) found in the hexasaccharides prepared by testicular hyaluronidase digestion of shark cartilage chondroitin sulfate D. Glycobiology. Mar. 1997;7(2):253-63.

Nader et al., Heparin sequences in the heparan sulfate chains of an endothelial cell proteoglycan. Proc Natl Acad Sci U S A. Jun. 1987;84(11):3565-9.

Nagasawa et al., Anticoagulant effect of low molecular weight fractions derived from a chemically modified heparin. Thromb Res. Nov. 15, 1991;64(4):521-5.

Norgard-Sumnicht et al., Exploring the outcome of genetic modifications of glycosylation in cultured cell lines by concurrent isolation of the major classes of vertebrate glycans. Glycobiology. Jul. 2000;10(7):691-700.

Petitou et al., Synthesis of thrombin-inhibiting heparin mimetics without side effects. Nature. Apr. 1, 1999;398(6726):417-22.

Petitou et al., Synthetic oligosaccharides having various functional domains: potent and potentially safe heparin mimetics. Bioorg Med Chem Lett. Apr. 19, 1999;9(8):1161-6.

Plaas et al., Glycosaminoglycan sulfation in human osteoarthritis. Disease-related alterations at the non-reducing termini of chondroitin and dermatan sulfate. J Biol Chem. May 15, 1998;273(20):12642-9.

Prabhakar et al., Chondroitinase ABC I from *Proteus vulgaris*: cloning, recombinant expression and active site identification. Biochem J. Feb. 15, 2005;386(Pt 1):103-12.

Prabhakar et al., Biochemical characterization of the chondroitinase ABC I active site. Biochem J. Sep. 1, 2005;390(Pt 2):395-405.

Rahbek-Nielsen et al., Glycopeptide profiling of human urinary erythropoietin by matrix-assisted laser desorption/ionization mass spectrometry. J Mass Spectrom. Sep. 1997;32(9):948-58.

Raman et al., Structural insights into biological roles of protein-glycosaminoglycan interactions. Chem Biol. Mar. 2005;12(3):267-77.

Raman et al., Glycomics: an integrated systems approach to structure-function relationships of glycans. Nat Methods. Nov. 2005;2(11):817-24.

Raman et al., Advancing Glycomics: Implementation Strategies at the Consortium for Functional Glycomics. Glycobiology. Feb. 14, 2006; [Epub ahead of print].

Ray et al. Glycoprotein Glycan Analysis; A new USP General Chapter. Slides of a lecture presented at the USP Conferece on Biological and Biotechnological Drug Substances and Products. Crystal City, Virginia. Nov. 20, 2003.

Razi et al., Structural and functional properties of heparin analogues obtained by chemical sulphation of *Escherichia coli* K5 capsular polysaccharide. Biochem J. Jul. 15, 1995;309 ( Pt 2):465-72.

Rush et al., Microheterogeneity of erythropoietin carbohydrate structure. Anal Chem. Apr. 15, 1995;67(8):1442-52.

Rush et al., Peptide mapping and evaluation of glycopeptide microheterogeneity derived from endoproteinase digestion of erythropoietin by affinity high-performance capillary electrophoresis. Anal Chem. Jul. 15, 1993;65(14):1834-42.

Sampaio et al., Effect of monensin on the sulfation of heparan sulfate proteoglycan from endothelial cells. J Cell Biochem. Sep. 1992;50(1):103-10.

Sasaki et al., Site-specific glycosylation of human recombinant erythropoietin: analysis of glycopeptides or peptides at each glycosylation site by fast atom bombardment mass spectrometry. Biochemistry. Nov. 15, 1988;27(23):8618-26.

Shukla et al., A novel role for 3-O-sulfated heparan sulfate in herpes simplex virus 1 entry. Cell. Oct. 1, 1999;99(1):13-22.

Simeon et al., Expression of glycosaminoglycans and small proteoglycans in wounds: modulation by the tripeptide-copper complex glycyl-L-histidyl-L-lysine-Cu(2+). J Invest Dermatol. Dec. 2000;115(6):962-8.

Smith et al., Archeological Preservation Research Laboratory Report 11. 1998:1-6.

Sobel et al., Heparins designed to specifically inhibit platelet interactions with von Willebrand factor. Circulation. Mar. 1, 1996;93(5):992-9.

Sugahara et al., Novel sulfated oligosaccharides containing 3-O-sulfated glucuronic acid from king crab cartilage chondroitin sulfate K. Unexpected degradation by chondroitinase ABC. J Biol Chem. Oct. 25, 1996;271(43):26745-54.

Toida et al., Enzymatic preparation of heparin oligosaccharides containing antithrombin III binding sites. J Biol Chem. Dec. 13, 1996;271(50):32040-7.

Tseng et al., Catalog-library approach for the rapid and sensitive structural elucidation of oligosaccharides. Anal Chem. Sep. 1, 1999;71(17):3747-54.

Tumova et al., Heparan sulfate proteoglycans on the cell surface: versatile coordinators of cellular functions. Int J Biochem Cell Biol. Mar. 2000;32(3):269-88.

Turnbull et al., A strategy for rapid sequencing of heparan sulfate and heparin saccharides. Proc Natl Acad Sci U S A. Mar. 16, 1999;96(6):2698-703.

Venkataraman et al., A stereochemical approach to pyranose ring flexibility: its implications for the conformation of dermatan sulfate. Proc Natl Acad Sci U S A. Jun. 21, 1994;91(13):6171-5.

Venkataraman et al., Fibroblast growth factors 1 and 2 are distinct in oligomerization in the presence of heparin-like glycosaminoglycans. Proc Natl Acad Sci U S A. Mar. 2, 1999;96(5):1892-7.

Vives et al., Sequence analysis of heparan sulphate and heparin oligosaccharides. Biochem J. May 1, 1999;339 ( Pt 3):767-73.

Vlodavsky et al., Mammalian heparanase: gene cloning, expression and function in tumor progession and metastasis. Nat Med. Jul. 1999;5(7):793-802.

Warnick et al., Purification of an unusual -glycuronidase from flavobacteria. Biochemistry. Feb. 15, 1972;11(4):568-72.

Weiler et al., Heparin and modified heparin inhibit complement activation in vivo. J Immunol. May 15, 1992;148(10):3210-5.

Yamada et al., Structural studies on the tri- and tetrasaccharides isolated from porcine intestinal heparin and characterization of heparinase/heparitinases using them as substrates. Glycobiology. Feb. 1994;4(1):69-78.

Yamada et al., Isolation of the porcine heparin tetrasaccharides with glucuronate 2-O-sulfate. Heparinase cleaves glucuronate 2-O-sulfate-containing disaccharides in highly sulfated blocks in heparin. J Biol Chem. Apr. 14, 1995;270(15):8696-705.

Yamada et al., Structural studies of octasaccharides derived from the low-sulfated repeating disaccharide region and octasaccharide serines derived from the protein linkage region of porcine intestinal heparin. Biochemistry. Jan. 12, 1999;38(2):838-47.

Yang et al., Glycosylation in human thyroglobulin: location of the N-linked oligosaccharide units and comparison with bovine thyroglobulin. Arch Biochem Biophys. Mar. 1, 1996;327(1):61-70.

Yates et al., 1H and 13C NMR spectral assignments of the major sequences of twelve systematically modified heparin derivatives. Carbohydr Res. Nov. 20, 1996;294:15-27.

Zhou et al., Uroplakin 1a is the urothelial receptor for uropathogenic *Escherichia coli*: evidence from in vitro FimH binding. J Cell Sci. Nov. 2001;114(Pt 22):4095-103.

Hooker et al., High resolution glycoform analysis of recombinant human interferon-gamma during batch cultures of Chinese hamster ovary cells. Animal Cell Technology: Basic & Applied Aspects, Proceedings of the Annual Meeting of the Japanese Association for Animal Cell Technology, 8th, Fukuoka, Nov. 6-10, 1995, University of Kent, Canterbury, UK. (Abstract only).

Packer et al., Proteome analysis of glycoforms: a review of strategies for the microcharacterization of glycoproteins separated by two-dimensional polyacrylamide gel electrophoresis. Electrophoresis. 1997; 18(3-4):452-460 (Abstract only).

Klausen et al., Analysis of the glycoforms of human recombinant factor VIIa by capillary electrophoresis and high-performance liquid chromatography. J of Chromatography. 1995; 718(1):195-202. (Abstract only).

Parekh, Glycoform analysis of glycoproteins, Methods in Enzymology (Guide to Techniques). 1994; 230:340-8. (Abstract only).

Kinoshita et al., Comparative studies on the analysis of glycosylation heterogeneity of sialic acid-containing glycoproteins using capillary electrophoresis. J of Chromatography. Jan. 14, 2000; 866(2):261-71. (Abstract only).

Yim et al., Capillary zone electrophoretic resolution of recombinant human bone morphogenetic protein 2 glycoforms. An investigation into the separation mechanisms for an exquisite separation. J of Chromatography. Nov. 17, 1995; 716(1-2):401-12. (Abstract only).

Pantazaki et al., Recent advances in the capillary electrophoresis of recombinant glycoproteins. Analytica Chimica Acta. 1999; 383(1-2):137-156. (Abstract only).

Cifuentes et al., Capillary isoelectric focusing of erythropoietin glycoforms and its comparison with flat-bed isoelectric focusing and capillary zone electrophoresis. J of Chromatography. 1999; 830(2):453-463. (Abstract only).

Taverna et al., Electrophoretic methods for process monitoring and the quality assessment of recombinant glycoproteins. Electrophoresis. 1998; 19(15):2572-2594. (Abstract only).

Goldman et al., Monitoring recombinant human interferon-gamma N-glycosylation during perfused fluidized-bed and stirred-tank batch culture of CHO cells. Biotechnology and Bioengineering. 1998; 60(5):596-607. (Abstract only).

Zhou et al., Application of capillary electrophoresis, liquid chromatography, electrospray-mass spectrometry, and matrix-assisted laser desorption/ionization—time of flight—mass spectrometry to the characterization of recombinant human erythropoietin. Electrophoresis. 1998; 19(13):2348-2355. (Abstract only).

Fukazawa, Sugar chain alterations of glycoproteins in spent culture media of human hepatocellular carcinoma cell lines analyzed by lectin-affinity electrophoresis. Okayama Igakkai Zasshi. 1998; 110(1-6):53-60. (Abstract only).

Van Dijk et al., Glycosylation of a1-acid glycoprotein (orosomucoid) in health and disease: occurrence, regulation and possible functional implications. Trends in Glycoscience and Glycotechnology. 1998; 10(53):235-245 (Abstract only).

Zhang et al., Quantitative analysis and process monitoring of site-specific glycosylation microheterogeneity in recombinant human interferon-g from Chinese hamster ovary cell culture by hydrophilic interaction chromatography. Journal of Chromatography, B: Biomedical Sciences and Applications. 1998; 712(1+2):73-82. (Abstract only).

Packer et al., Analyzing glycoproteins separated by two-dimensional gel electrophoresis. Electrophoresis. 1998; 19(6):981-988. (Abstract only).

Routier et al., Quantitation of the different oligosaccharides of human serum 1gG from patients with rheumatoid arthritis: a critical evaluation of different methods. Journal of Immunological Methods. 1998; 213(2):113-130. (Abstract only).

Novotny, Capillary electrophoresis of carbohydrates. Chemical Analysis (High-Performance Capillary Electrophoresis). 1998; 146:729-765. (Abstract only).

Kleindienst et al., Capillary electrophoresis of peptides and proteins in fused-silica capillaries coated with derivatized polystyrene nanoparticles. Electrophoresis. 1998; 19(2):262-269. (Abstract only).

Wang et al., Mass spectrometric characterization and glycosylation profile of bovine pancreatic bile salt-activated lipase. Protein Expression and Purification. 1998; 12(2):259-268. (Abstract only).

Butters et al., Structural characterization of the N-linked oligosaccharides derived from HIV gp120 expressed in lepidopteran cells. Glycoconjugate Journal. 1998; 15(1):83-88. (Abstract only).

Bateman et al., Characterization of protein glycoforms by capillary-zone electrophoresis-nanoelectrospray mass spectrometry. J of Chromatography. 1998; 794(1+2):327-344. (Abstract only).

Oda et al., Capillary electrophoresis-based separation of transferrin sialoforms in patients with carbohydrate-deficient glycoprotein syndrome. Electrophoresis. 1997; 18(10):1819-1826. (Abstract only).

Karlsson et al., The glycosylation of rat intestinal Muc2 mucin varies between rat strains and the small and large intestine. A study of O-linked oligosaccharides by a mass spectrometric approach. Journal of Biological Chemistry. 1997;272(43):27025-27034. (Abstract only).

Hoffmann et al., Molecular characterization of b-trace protein in human serum and urine: a potential diagnostic marker for renal diseases. Glycobiology. 1997; 7(4):499-506. (Abstract only).

Yamada et al., Structural changes of immunoglobulin G oligosaccharides with age in healthy human serum. Glycoconjugate Journal. 1997; 14(3):401-405. (Abstract only).

Author Not Listed, Analysis of human serum transferrin glycoforms. LC-GC (1997), 15(4), 370.

Hsu et al., Differential N-glycan patterns of secreted and intracellular IgG produced in Trichoplusia ni cells. Journal of Biological Chemistry. 1997; 272(14):9062-9070. (Abstract only).

Iourin et al., The identification of abnormal glycoforms of serum transferrin in carbohydrate deficient glycoprotein syndrome type I by capillary zone electrophoresis. Glycoconjugate Journal. 1996; 13(6):1031-1042. (Abstract only).

Morris et al., Gender-specific glycosylation of human glycodelin affects its contraceptive activity. Journal of Biological Chemistry. 1996; 271(50):32159-32167. (Abstract only).

Yang et al., Capillary isoelectric focusing-electrospray ionization mass spectrometry for transferrin glycoforms analysis. Analytical Biochemistry. 1996; 243(1):140-149. (Abstract only).

Chen, Capillary electrophoretic analysis of glycoform of glycoproteins. Fushun Shiyou Xueyuan Xuebao. 1996; 16(3):68-69. (Abstract only).

Iwase et al., Estimation of the number of O-linked oligosaccharides per heavy chain of human serum IgA1 by matrix-assisted laser desorption ionization time-of-flight mass spectrometry (MALDI-TOFMS) analysis of the hinge glycopeptide. Journal of Biochemistry (Tokyo). 1996; 120(2):393-397. (Abstract only).

Iwase et al., Abudance of Galb1,3GalNAc in O-linked oligosaccharide on hinge region of polymerized IgA1 and heat-aggregated IgA1 from normal human serum. Journal of Biochemistry (Tokyo). 1996; 120(1):92-97. (Abstract only).

Honda, Application of capillary electrophoresis to the analyses of carbohydrates and glycoproteins. Seibutsu Butsuri Kagaku. 1996; 40(3):147-154. (Abstract only).

Thornton et al., Respiratory mucins: identification of core proteins and glycoforms. Biochemical Journal. 1996; 316(3):967-975. (Abstract only).

Ogonah et al., Characterization and analysis of human interferon-g glycoforms produced in baculovirus infected *Spodoptera frugiperda* (Sf9) and *Estigmens acrea* (Ea) cell lines. Animal Cell Technology; Developments towards the 21st Century, [Proceedings of the Meeting], Veldhoven, Neth.,.Sep. 12-16, 1994. (Abstract only).

Hanisch et al., MUCI glycoforms n breast cancer. Cell line T47D as a model for carcinoma-associated alterations of O-glycosylation. Euripean Journal of Biochemistry. 1996;236(1):318-27. (Abstract only).

Burlingame, Characterization of protein glycosylation by mass spectrometry. Current Opinion in Biotechnology. 1996; 7(1):4-10. (Abstract only).

Kelly et al., Development of electrophoretic conditions for the characterization of protein glycoforms by capillary electrophoresis-electrospray mass spectrometry. Journal of Chromatography. 1996; 720(1+2):409-27. (Abstract only).

Kakehi et al., Analysis of glycoproteins, glycopeptides and glycoprotein-derived oligosaccharides by high-perfomance capillary electrophoresis. Journal of Chromatography. 1996; 720(1+2):377-93. (Abstract only).

Legaz et al., Effect of polyamines on the separation of ovalbumin glycoforms by capillary electrophoresis. Journal of Chromatography. 1996; 719(1):159-70. (Abstract only).

Roberts et al., An Integrated Strategy for Structural Characterization of the Protein and Carbohydrate Components of Monoclonal Antibodies: Application to Anti-Respiratory Syncytial Virus MAb. Analytical Chemistry. 1995; 67(20):3613-25. (Abstract only).

Mackiewicz et al., Glycoforms of serum a1-acid glycoprotein as markers of inflammation and cancer. Glycoconjugate Journal. 1995; 12(3):241-7. (Abstract only).

Van Dijk et al., a1-Acid glycoprotein (orosomucoid): pathophysiological changes in glycosylation in relation to its function. Glycoconjugate Journal. 1995; 12(3):227-33. (Abstract only).

De Reggi et al., The glycan moiety of human pancreatic lithostathine. Structure characterization and possible pathophysiological implications. European Journal of Biochemistry. 1995; 230(2):503-10. (Abstract only).

Pirie-Shepherd et al., Sialic acid content of plasminogen 2 glycoforms as a regulator of fibrinolytic activity. Isolation, carbohydrate analysis, and kinetic characterization of six glycoforms of plasminogen 2. Journal of Biological Chemistry. 1995; 270(11):5877-81. (Abstract only).

Wu et al., Characterization of neutralization epitopes in the V2 region of human immunodeficiency virus type 1 gp120 and the role of glycosylation in the correct folding of the V1/V2 domain. Journal of Virology. 1995; 69(4):2271-8. (Abstract only).

Ogonah et al., Analysis of human interferon-g glycoforms produced in baculovirus infected insect cells by matrix assisted laser desorption spectrometry. Biochemical Society Transactions. 1995; 23(1):100S. (Abstract only).

Jenkins, Monitoring and control of recombinant glycoprotein heterogeneity in animal cell cultures. Biochemical Society Transactions. 1995; 23(1):171-5. (Abstract only).

Van Der Linden et al., Preparative affinity electrophoresis of different glycoforms of serum glycoproteins: Application for the Study of inflammation-induced expression of sialyl-Lewisx groups on a1-acid glycoprotein (orosomucoid). Glycosylation & Disease. 1994; 1(1):45-52. (Abstract only).

Andersen et al., Monosaccharide and oligosaccharide analysis of isoelectric focusing-separated and blotted granulocyte colony-stimulating factor glycoforms using high-pH anion-exchange chromatography with pulsed amperometric detection. Glycobiology. 1994; 4(4):459-67. (Abstract only).

Medzihradszky et al., Characterization of protein N-glycosylation by reversed-phase microbore liquid chromatography/electrospray mass spectrometry, complementary mobile phases, and sequential exoglycosidase digestion. Journal of the American Society for Mass Spectrometry. 1994; 5(5):350-8. (Abstract only).

Pedersen et al., Characterization of proteinase A glycoforms from recombinant *Saccharomyces cerevisiae*. Biotechnology and Applied Biochemistry. 1993; 18(3):377-88. (Abstract only).

Mueller et al., Characterization and direct glycoform profiling of a hybrid plasminogen activator by matrix-assisted laser desorption and electrospray mass spectrometry; correlation with high-performance liquid chromatographic and nuclear magnetic resonance analyses of rhe released glycans. Biological Mass Spectrometry. 1994; 23(6):330-8. (Abstract only).

Duffin et al., Identification and oligosaccharide structure analysis of rhodopsin glycoforms containing galactose and sialic acid. Glycobiology. 1993; 3(4):365-380. (Abstract only).

Mackiewicz et al., Glycoforms of a1-acid glycoprotein as disease markers. Acute Phase Proteins. 1993; 651-61. (Abstract only).

Rudd et al., Glycoforms modify the dynamic stability and functional activity of an enzyme. Biochemistry. 1994; 33(1):17-22. (Abstract only).

Clogston et al., Glycosidase digestion, electrophoresis and chromatographic analysis of recombinant human granulocyte colony-stimulating factor glycoforms produced in Chinese hamster ovary cells. Journal of Chromatography. 1993; 637(1):55-62. (Abstract only).

Coco-Martin et al., Analysis of glycoforms present in two mouse IgG2a monoclonal antibody preparations. Journal of Immunological Methods. 1992; 155(2):241-8. (Abstract only).

Iwase et al., Analysis of glycoform of O-glycan from human myeloma immunoglobulin A1 by gas-phase hydrazinolysis following pyridylamination of oligosaccharides. Analytical Biochemistry. 1992; 206(1):202-5. (Abstract only).

Rudd et al., Separation and analysis of the glycoform populations of ribonuclease B using capillary electrophoresis. Glycoconjugate Journal. 1992; 9(2):86-91. (Abstract only).

Treuheit et al., Analysis of the five glycosylation sites of human a1-acid glycoprotein. Biochemical Journal. 1992; 283(1):105-12. (Abstract only).

Yim, Fractionation of the human recombinant tissue plasminogen activator (rtPA) glycoforms by high-performance capillary zone electrophoresis and capillary isoelectric focusing. Journal of Chromatography. 1991; 559(1-2):401-10. (Abstract only).

Hefta et al., Sequence and glycosylation site identity of two distinct glycoforms of nonspecific cross-reacting antigen as demonstrated by sequence analysis and fast atom bombardment mass spectrometry. Journal of Biological Chemistry. 1990; 265(15):8618-26. (Abstract only).

O'Hare et al., Glycoforms of human serum proteins identified by *Ricinus communis* lectin. Biochemical Society Transactions. 1990; 18(2):323. (Abstract only).

Janska et al., The lower molecular weight acid phosphatase from the frog liver: isolation of homogeneous AcPase III and IV representing glycoforms with different bioactivity. Comparative Biochemistry and Physiology, Part B: Biochemistry & Molecular Biology. 1989; 92B(2):341-6. (Abstract only).

Zeng et al., Characterization and analysis of a novel glycoprotein from snake venom using liquid chromatography-electrospray mass spectrometry and Edman degradation. European Journal of Biochemistry/FEBS. Dec. 1999; 266(2):352-8. (Abstract only).

Thalmann et al., Uronic acid-containing glycosaminoglycans and keratan sulfate are present in the tectorial membrane of the inner ear: functional implications. Arch Biochem Biophys. Dec. 1993;307(2):391-6.

Abushoufa et al. "The development of a sialic acid specific lectin-immunoassay for the measurement of human chorionic gonadotrophin glycoforms in serum and its application in normal Down's syndrome pregnancies", *Clinical endocrinology*, vol. 52, No. 4, (Apr. 2000) 499-508. Abstract only.
Apffel et al. "Application of new analytical technology to the production of a 'well-characterized biological'", Developments in biological standardization, vol. 96 (1998) 11-25. Abstract only.
Bihoreau et al. "Combination of capillary electrophoresis and matrix-assisted laser desorption ionization mass spectrometry for glycosylation analysis of a human monoclonal anti-Rhesus(D) antibody", *J Chromatogr B Biomed Sci Appl.*, Sep. 12, 1997; 697(1-2):123-33.
Carlson et al., Biosynthesis of abnormally glycosylated alpha 1-antitrypsin by a human hepatoma cell line Hepatology. Mar.-Apr. 1984;4(2):235-41.
Coulombe et al., Elucidating the early stages of keratin filament assembly. J Cell Biol. Jul. 1990;111(1):153-69.
Dennis et al., Beta 1-6 branching of Asn-linked oligosaccharides is directly associated with metastasis. Science. May 1, 1987;236(4801):582-5.
Dennis et al., "Glycoprotein glycosylation and cancer progression", *Biochim Biophys Acta.*, Dec. 6, 1999; 1473(1):21-34.
Feldman et al., Identification of a linear heparin binding domain for human respiratory syncytial virus attachment glycoprotein G. J Virol. Aug. 1999;73(8):6610-7.
Ferens-Sieczkowska et al. "Haptoglobin glycoforms in a case of carbohydrate-deficient glycoprotein syndrome", *Glycoconjugate J.*, Oct. 1999; 16(10):573-7.
Fernandes et al. "Beta 1-6 branched oligosaccharides as a marker of tumor progression in human breast and colon neoplasia", *Cancer Res.*, Jan. 15, 1991; 51(2):718-23.
Gerwig et al. "Analysis of glycoprotein-derived glycopeptides", *Proteomics in Functional Genomics*, EXS, Birkhaeuser Verlag 2000; 88:159-86.
Hahn et al., Growth-associated glycosylation of transferrin secreted by HepG2 cells. J Biol Chem. Nov. 25, 1992;267(33):23982-7.
Hanley et al., Biosynthesis and processing of rat haptoglobin. J Biol Chem. Jun. 25, 1983;258(12):7858-69.
Harvey "Identification of cleaved oligosaccharides by matrix-assisted laser desorption/ionization", *Methods Mol. Biol.*, vol. 61 (1996) 243-53.
Harvey, "Quantitative aspects of the matrix-assisted laser desorption mass spectrometry of complex oligosaccharides", *Rapid Commun Mass Spectrom*, vol. 7, No. 7 (Jul. 1993) 614-9.
Horner et al., Heterogeneity of rat skin heparin chains with high affinity for antithrombin. Biochem J. Jun. 15, 1987;244(3):693-8.
Iwase et al. "Application of matrix-assisted laser desorption ionization time-of-flight mass spectrometry to the analysis of glycopeptide-containing multiple O-linked oligosaccharides", *Journal of Chromatography, B, Biomedical sciences and applications*, vol. 709, No. 1 (May 8, 1998), 145-9. Abstract only.
Joao et al. "Effects of glycosylation on protein structure and dynamics in ribonuclease B and some of its individual glycoforms," *Eur. J. Biochem.*, Nov. 15, 1993; 218(1):239-44.
Jørgensen et al., Up-regulation of the oligosaccharide sialyl LewisX: a new prognostic parameter in metastatic prostate cancer. Cancer Res. May 1, 1995;55(9):1817-9.
Juhasz et al. "Utility of non-covalent complexes in the matrix-assisted laser desorption ionization mass spectrometry of heparin-derived oligosaccharides", *Carbohydr Res.*, Apr. 30, 1995; 270(2):131-47.
Juhasz et al., "Mass spectrometric molecular-weight determination of highly acidic compounds of biological significance via their complexes with basic polypeptides", *Proc. Natl. Acad. Sci. USA*, May 1994; 91:4333-7.
Kannagi et al., Carbohydrate-mediated cell adhesion involved in hematogenous metastasis of cancer. Glycoconj J. Aug. 1997;14(5):577-84.
Kim et al., Perspectives on the significance of altered glycosylation of glycoproteins in cancer. Glycoconj J. Aug. 1997;14(5):569-76.
Kishibe et al., Structural requirements of heparan sulfate for the binding to the tumor-derived adhesion factor/angiomodulin that induces cord-like structures to ECV-304 human carcinoma cells. J Biol Chem. May 19, 2000;275(20):15321-9.
Kreuger et al., "Characterization of fibroblast growth factor 1 binding heparan sulfate domain," *Glycobio.* (1999) 9(7):723-9.
Lacko et al. Characterization of recombinant human plasma lecithin: cholesterol acyltransferase (LCAT): N-linked carbohydrate structures and catalytic properties, *J Lipid Res.*, Apr. 1998; 39(4):807-20.
Matsuura et al. "Human α-galactosidase A: characterization of the N-linked oligosaccharides on the intracellular and secreted glycoforms overexpressed by Chinese hamster ovary cells", *Glycobiology*, vol. 8, No. 4, (1998) 329-339.
Merry, "Current techniques in protein glycosylation analysis. A guide to their application", *Acta Biochimica Polonica*, 1999; 46(2):303-14.
Nesheim et al., Dependence of antithrombin III and thrombin binding stoichiometries and catalytic activity on the molecular weight of affinity-purified heparin. J Biol Chem. Mar. 5, 1986;261(7):3214-21.
Nimtz "Structural characterization of the oligosaccharide chains of native and crystallized boar seminal plasma spermadhesin PSP-I and PSP-II glycoforms", *European journal of biochemistry/FEBS*, vol. 265, No. 2 (Oct. 1999) 703-18.
Nugent, Heparin sequencing brings structure to the function of complex oligosaccharides. PNAS Sep. 12, 2000; 97(19):10301-3.
Odani "Direct evidence for decreased sialylation and galactosylation of human serum IgA1 Fc O-glycosylated hinge peptides in IgA nephropathy by mass spectrometry", *Biochemical and Biophysical Research Communications*, vol. 271, No. 1, (Apr. 29, 2000) 268-74. Abstract only.
Orntoft et al., "Clinical aspects of altered glycosylation of glycoproteins in cancer", *Electrophoresis*, Feb. 1999; 20(2):362-71.
Papac et al., A high-throughput microscale method to release N-linked oligosaccharides from glycoproteins for matrix-assisted laser desorption/ionization time-of-flight mass spectrometric analysis. Glycobiology. May 1998;8(5):445-54.
Parthasarathy et al., "Oligosaccharide sequence of human breast cancer cell heparan sulfate with high affinity for laminin," *J. Biol. Chem.* (1998) 273(33):21111-4.
Pierce et al., Regulation of N-acetylglucosaminyltransferase V and Asn-linked oligosaccharide beta(1,6) branching by a growth factor signaling pathway and effects on cell adhesion and metastatic potential. Glycoconj J. Aug. 1997;14(5):623-30.
Pili et al., The alpha-glucosidase I inhibitor castanospermine alters endothelial cell glycoslyation, prevents angiogenesis, and inhibits tumor growth. Cancer Res. Jul. 1, 1995;55(13):2920-6.
Powell et al. "Natural ligands of the B cell adhesion molecule CD22β carry N-linked oligosaccharides with α-2,6-linked sialic acids that are required for recognition", *J. Biol. Chem.*, Apr. 5, 1993; 268(10):7019-27.
Prakash et al., "Glycotyping of prostate specific antigen", *Glycobiology*, Feb. 2000; 10(2):173-6.
Raju et al., "Species-specific variation in glycosylation of IgG: evidence for the species-specific sialylation and branch-specific galactosylation and importance for engineering recombinant glycoprotein therapeutics", Glycobiology, May 2000; 10(5):477-86.
Sasaki et al., "Structural basis and potential role of heparin/heparan sulfate binding to the angiogenesis inhibitor endostatin," *Embo. J.* (1999) 18(22):6240-8.
Scanlin et al., "Terminal glycosylation and disease: influence on cancer and cystic fibrosis", *Glycoconj J.*, Jul.-Sep. 2000; 17(7-9):617-26.
Seelentag et al., Expression of CD44 isoforms and beta 1,6-branched oligosaccharides in human malignant melanoma is correlated with tumor progression but not with metastatic potential. J Cutan Pathol. Apr. 1997;24(4):206-11.
Shimodaira et al. "Carcinoma-associated expression of core 2 beta-1,6-N-acetylglucosaminyltransferase gene in human colorectal cancer: role of O-glycans in tumor progression", *Cancer Res.*, Dec. 1, 1997; 57(23):5201-6.
Taketa "Characterization of sugar chain structures of human alpha-fetoprotein by lectin affinity electrophoresis", ibarahp@oka.urban.ne.jp., *Electrophoresis*, vol. 19, No. 15, (Nov. 1998) 2595-602. Abstract only.
Volpi N. et al. "Fast moving" and "slow moving" heparins, dermatan sulfate, and chondroitin sulfate: qualitative and quantitative analysis by agarose-gel electrophoresis *Carb. Res.*, 247:263-278, 1993.
Yousefi et al., Increased UDP-GlcNAc:Galbeta1-3GalNAc-R (GlcNA to GalNAc) beta-1,6-N-acteylglucosaminyltransferase activity in metastatic murine tumor cell lines. Control of polylactosamine synthesis. J Biol Chem. Jan. 25, 1991;266(3):1772-82.

Ernst, S. et al., "Direct evidence for a predominantly exolytic processive mechanism for depolymerization of heparin-like glycosaminoglycans by heparinase I", *Proc. Natl. Acad. Sci. USA*, Apr. 1998, pp. 4182-4187.

Hayes, B., "Prototeins", *American Scientist*, May-Jun. 1998, pp. 216-221, vol. 86.

Rudd, P.M. et al., "Oligosaccharide sequencing technology", *Nature*, Jul. 10, 1997, pp. 205-207, vol. 388.

Yan, J. F. et al., "Prime Numbers and Amino Acid Code: Analogy in Coding Properties", *J. Theor. Biol.*, 1991, pp. 333-341, vol. 151, Academic Press Limited.

Zhao, Y. et al., "Rapid, sensitive structure analysis of oligosaccharides", *Proc. Natl. Acad. Sci. USA*, Mar. 1997, pp. 1629-1633, vol. 94, Chemistry.

Alderman, C. et al., "Continuous Subcutaneous Heparin Infusion for Treatment of Trousseau's Syndrome", *Ann Pharmacother*, Jul.-Aug. 1995, 29:(7-80:710-713.

Baumann, U. et al., "Three-dimensional structure of the alkaline protease of Pseudomonas aeruginosa: a two-domain protein with a calcium binding parallel beta roll motif", *The EMBO Journal*, vol. 12, No. 9, pp. 3357-3364, 1993.

Berstein, H. et al., "Immobilized Heparin Lyase System for Blood Deheparinization", *Methods in Enzymology*, vol. 137, pp. 515-529, 1998.

Cardin, A. D. et al., "Molecular Modeling of Protein-Glycosaminoglycan interactions", *Arteriosclerosis*, vol. 9, No. 1, Jan./Feb. 1986, pp. 21-32.

Cohen, F. E., "The Parallel β Helix of Pectate Lyase C; Something to Sneeze At", *Science*, vol. 260, Jun. 4, 1993, pp. 1444-1445.

Comfort, A. R. et al., "Immobilized Enzyme Cellulose Hollow Fibers: III. Physical Properties and *In Vitro* Biocompatility", *Biotechnology and Bioengineering*, vol. 34, pp. 1383-1390, 1989.

Feingold, D. S. et al., Conformational aspects of the reaction mechanisms of polysaccharide lyases and epimerases, *FEBS Letters*, vol. 223, No. 2, Nov. 1987, pp. 207-211.

Franklin, M. J. et al., "Pseudomonas Aeruginosa AlgG is a Polymer Level Alginate C5-Mannuronan Epimerase", *Journal of Bacteriology*, vol. 176, No. 7, Apr. 1994, pp. 1821-1830.

Gacesa, P., "Alginate-modifying anzymes - A proposed unified mechanism of action for the lyases and epimerases", *FEBS Letters*, vol. 212, No. 21, Feb. 1987, pp. 199-202.

Godavarti R. et al., "Heparinase I from Flavobacterium heparinum. Identification of a Critical Histidine Residue Essential for Catalysis as Probed by Chemical Modification and Site-Directed Mutagensis", *Biochemistry*, vol. 35, No. 21, 1996, pp. 6846-6852.

Enriquez-Harris, P. et al., "Growth Factors and the Extracellular Matrix", *Meeting Report*, Trends in Cell Biology, 1994.

Hart, G. W., "Glycosylation", *Current Opinion in Cell Biology*, 1992, 4:1017-1023.

Higuchi, R., "Recombinant PCT", *PCR Protocols: A Guide to Methods and Applications, Academic Press, Inc.*, 1990, pp. 177-183.

Huang, J. N., "Low-Molecular-Weight Heparins", *Coagulation Disorders*, vol. 12, No. 6, Dec. 1998, pp. 1251-1277.

Jackson, R. L. et al., "Glycosaminoglycans: Molecular Properties, Protein Interactions, and role In Physiological Processes", *Reviews*, vol. 71, No. 2, Apr. 1991, pp. 481-539.

Kakkar, A. et al., "Venous Thromboembolism and Cancer", *Baollieres Clin Haematol*, Sep. 1998, 11(3):675-687.

Kretsinger, R. H. et al., "Structure and Evolution of Calcium-Modulated Proteins", *CRC Critical Reviews in Biochemistry*, vol. 8, Issue 2, Jul. 1980, pp. 119-174.

Leckband, D. et al., "An Approach for the Stable Immobilization of Proteins", *Biotechnology and Bioengineering*, (1991), vol. 37, pp. 227-237.

Leckband, D. et al., "Characterization of the Active Site Of Heparinase", Abstracts for Papers from the Fourth Chemical Congress of North America, vol. 202, No. 1, Aug. 1991, New York, pp. a56.

Lewin, B., "Cells Obey the Laws of Physics and Chemistry", *Genes V*, 1994, p. 13.

Linhardt, R. J. et al., "Review Polysaccharide Lyases", *Applied Biochemistry and Biotechnology*, vol. 12, 1986, pp. 135-176.

Linhardt, R. J. et al., "Examination of the Substrate Specificity of Heparan Sulfate Lyases", *Biochemistry*, vol. 29, No. 10, 1990, pp. 2611-2617.

Linhardt, R. J. et al., "Production and Chemical Processing of Low Molecular Weight Heparins", *Seminars in Thrombosis and Hemostasis*, vol. 25, Suppl. 3, 1999, pp. 5-16.

Lohse, D. L. et al., "Purification and Characterization of Heparin Lyases from *Flavobacterium heparinum*", *The Journal of Biological Chemistry*, vol. 267, No. 34, Issue of Dec. 5, 1992, pp. 24347-24355.

Lustig, F. et al., "Alternative Splicing Determines the Binding of Platelet-Derived Growth Factor (PDGF-AA) to Glycosaminoglycans", *Biochemistry*, vol. 35, No. 37, 1996, pp. 12077-12085.

Sasisekharan, R. et al., "Cloning and expression of heparinase I gene from *Flavobacterium heparinum*", *Proc Natl Acad Sci USA*, vol. 90, pp. 3660-3664, Apr. 1993.

Sasisekharan, R. et al., "Heparinase inhibits neovascularization", Proc Natl Acad Sci USA, vol. 91, pp. 1524-1528, Feb. 1994.

Sasisekharan, R. et al., "Heparinase I from *Flavobacterium heparinum*: The Role of the Cysteine residue in Ctalysis as Probed by Chemical Modification and Site-Directed Mautagenesis", Biochemistry, vol. 34, No. 44, pp. 14441-14448, 1995.

Sasisekharan, R. et al., "Heparinase I from Flavobacterium", *The Journal of Bioliogical Chemistry*, vol. 271, No. 6, Issue Feb. 9, 1996, pp. 3124-3131.

Shriver, Z. et al., "Heparinase II from Flavobacterium heparinum: Role of Histidine Residues in Enzymatic Activity as Probed by Chemical Modification and Site-Directed Mutagenesis", *The Journal of Biological Chemistry*, vol. 273, No. 17, Apr. 1998, pp. 10160-10167.

Shriver, Z. et al., "Herparinase II from Flavorbacterium heparinum: Role of Cysteine in Enzymatic Activity as Probed by Chemical Modification and Site-Directed Mutagenesis," *The Journal of Biological Chemistry*, vol. 273, No. 36, Sep. 1998, pp. 22904-22912.

Valentine, K. A. et al., "Low-Molecular-Weight Heparin Therapy and Mortality", *Seminars in Thrombosis and Hemostasis*, vol. 23, No. 2, 1997, pp. 173-178.

Yang, V. C. et al., "Purification and Characterization of Heparinase from *Flavobacterium heparinum*", *The Journal of Biological Chemistry*, vol. 260, No. 3, Feb. 1985, pp. 1849-1857.

Yoder, M. D. et al., "Unusual structural features in the parallel β-helix in pectate lyases", *Structure*, Dec. 1993, vol. 1, No. 4, pp. 241-251.

Yoder, M. D. et al., "New Domain Motif: The Structure of Pectate Lyase C., a Secreted Plant Virulence Factor", *Science*, vol. 260, pp. 1503-1506, Jun. 4, 1993.

Zucharski, L. et al., "Blood Coagulation Activation in Cancer: Challenges for Cancer Treatment", *Hamostaseologie*, 1995, 15:14-20.

* cited by examiner

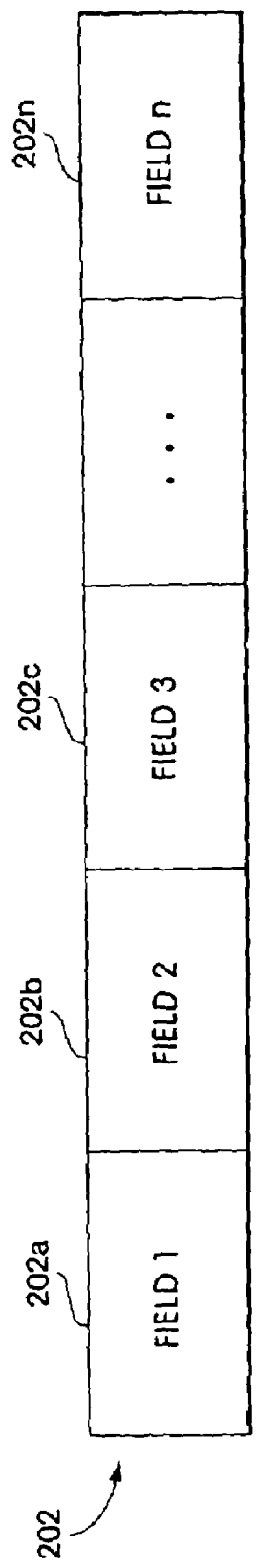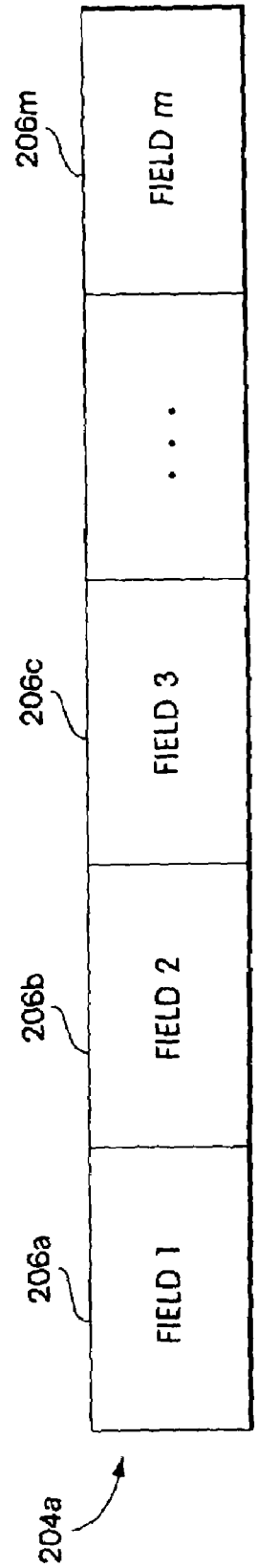

METHOD FOR ANALYZING POLYSACCHARIDES

RELATED APPLICATION

This application claims priority under 35 U.S.C. §119 to U.S. Provisional Patent Application Nos. 60/130,747, filed Apr. 23, 1999, 60/130,792, filed Apr. 23, 1999, 60/159,939, filed Oct. 14, 1999, and 60/159,940, filed Oct. 14, 1999, each of which are incorporated herein by reference in their entirety.

GOVERNMENT SUPPORT

This invention was made with government support under grant number 301-R01-GM057073-08S1 and awarded by the National Institute of Health. The government has certain rights in this invention.

BACKGROUND

Various notational systems have been used to encode classes of chemical units. In such systems, a unique code is assigned to each chemical unit in the class. For example, in a conventional notational system for encoding amino acids, a single letter of the alphabet is assigned to each known amino acid. A polymer of chemical units can be represented, using such a notational system, as a set of codes corresponding to the chemical units. Such notational systems have been used to encode polymers, such as proteins, in a computer-readable format. A polymer that has been represented in a computer-readable format according to such a notational system can be processed by a computer.

Conventional notational schemes for representing chemical units have represented the chemical units as characters (e.g., A, T, G, and C for nucleic acids), and have represented polymers of chemical units as sequences or sets of characters. Various operations may be performed on such a notational representation of a chemical unit or a polymer comprised of chemical units. For example, a user may search a database of chemical units for a query sequence of chemical units. The user typically provides a character-based notational representation of the sequence in the form of a sequence of characters, which is compared against the character-based notational representations of sequences of chemical units stored in the database. Character-based searching algorithms, however, are typically slow because such algorithms search by comparing individual characters in the query sequence against individual characters in the sequences of chemical units stored in the database. The speed of such algorithms is therefore related to the length of the query sequence, resulting in particularly poor performance for long query sequences.

SUMMARY

In one aspect, the invention is directed to a notational system for representing polymers of chemical units. The notational system is referred to as Property encoded nomenclature (PEN). According to one embodiment of the notational system, a polymer is assigned an identifier that includes information about properties of the polymer. For example, in one embodiment, properties of a disaccharide are each assigned a binary value, and an identifier for the disaccharide includes the binary values assigned to the properties of the disaccharide. In one embodiment, the identifier is capable of being expressed as a number, such as a single hexadecimal digit. The identifier may be stored in a computer readable medium, such as in a data unit (e.g., a record or a table entry) of a polymer database. Polymer identifiers may be used in a number of ways. For example, the identifiers may be used to determine whether properties of a query sequence of chemical units match properties of a polymer of chemical units. One application of such matching is to quickly search a polymer database for a particular polymer of interest or for a polymer or polymers having specified properties.

In one aspect, the invention is directed to a data structure, tangibly embodied in a computer-readable medium, representing a polymer of chemical units. In another aspect, the invention is directed to a computer-implemented method for generating such a data structure. The data structure may include an identifier that may include one or more fields for storing values corresponding to properties of the polymer. At least one field may be a non-character-based field. Each field may be capable of storing a binary value. The identifier may be a numerical identifier, such as a number that is representable as a single-digit hexadecimal number.

The polymer may be any of a variety of polymers. For example, (1) the polymer may be a polysaccharide and the chemical units may be saccharides; (2) the polymer may be a nucleic acid and the chemical units may be nucleotides; or (3) the polymer may be a polypeptide and the chemical units may be amino acids.

The properties may be properties of the chemical units in the polymer. For example, the properties may include charges of chemical units in the polymer, identities of chemical units in the polymer, confirmations of chemical units in the polymer, or identities of substituents of chemical units in the polymer. The properties may be properties of the polymer that are not properties of any individual chemical unit within the polymer. Example properties include a total charge of the polymer, a total number of sulfates of the polymer, a dye-binding of the polymer, a mass of the polymer, compositional ratios of substituents, compositional ratios of iduronic versus glucuronic, enzymatic sensitivity, degree of sulfation, charge, and chirality.

In another aspect, the invention is directed to a computer-implemented method for determining whether properties of a query sequence of chemical units match properties of a polymer of chemical units. The query sequence may be represented by a first data structure, tangibly embodied in a computer-readable medium, including an identifier that may include one or more bit fields for storing values corresponding to properties of the query sequence. The polymer may be represented by a second data structure, tangibly embodied in a computer-readable medium, including an identifier that may include one or more bit fields for storing values corresponding to properties of the polymer. The method may include acts of generating at least one mask based on the values stored in the one or more bit fields of the first data structure, performing at least one binary operation on the values stored in the one or more bit fields of the second data structure using the at least one mask to generate at least one result, and determining whether the properties of the query sequence match the properties of the polymer based on the at least one result. The chemical units may, for example, be any of the chemical units described above. Similarly, the properties may be any of the properties described above.

In one embodiment, the act of generating includes an act of generating the at least one mask as a sequence of bits that is equivalent to the values stored in the one or more bit fields of the first data structure. In another embodiment, the act of generating includes an act of generating the at least one mask as a sequential repetition of the values stored in the one or more bit fields of the first data structure.

In a further embodiment, the at least one mask includes a plurality of masks and the act of performing at least one binary operation includes acts of performing a logical AND operation on the values stored in the one or more bit fields of the second data structure using each of the plurality of masks to generate a plurality of intermediate results, and combining the plurality of intermediate results using at least one logical OR operation to generate the at least one result. In one embodiment, the act of determining includes an act of determining that the properties of the query sequence match the properties of the polymer when the at least one result has a non-zero value. In a further embodiment, the at least one binary operation includes at least one logical AND operation.

In another aspect, the invention is directed to a database, tangibly embodied in a computer-readable medium, for storing information descriptive of one or more polymers. The database may include one or more data units (e.g., records or table entries) corresponding to the one or more polymers, each of the data units may include an identifier that may include one or more fields for storing values corresponding to properties of the polymer.

In another embodiment, the invention is directed to a data structure, tangibly embodied in a computer-readable medium, representing a chemical unit of a polymer. The data structure may comprise an identifier including one or more fields. Each field may be for storing a value corresponding to one or more properties of the chemical unit. At least one field may store a non-character-based value such as, for example, a binary or decimal value.

Other aspects of the invention include the various combinations of one or more of the foregoing aspects of the invention, as well as the combinations of one or more of the various embodiments thereof as found in the following detailed description or as may be derived therefrom. It should be understood that the foregoing aspects of the invention also have corresponding computer-implemented processes which are also aspects of the present invention. It should also be understood that other embodiments of the present invention may be derived by those of ordinary skill in the art both from the following detailed description of a particular embodiment of the invention.

DETAILED DESCRIPTION

The present invention will be better understood in view of the following detailed description of a particular embodiment thereof, taken in conjunction with the attached drawings. All references cited herein are hereby expressly incorporated by reference.

Figure 1:
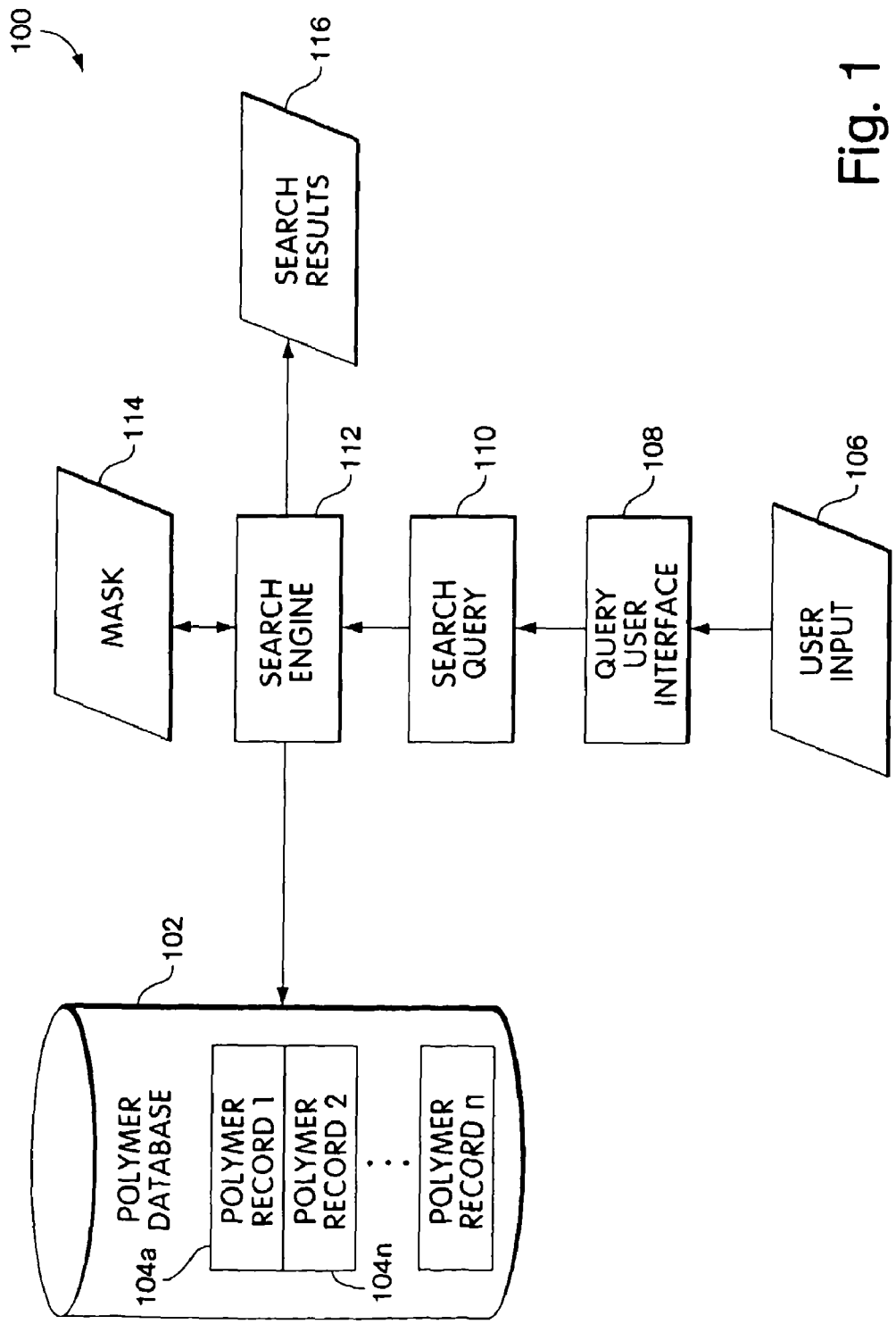
FIG. 1 is a block diagram illustrating an example of a computer system for storing and manipulating polymer information.

FIG. 1 shows an example of a computer system 100 for storing and manipulating polymer information. The computer system 100 includes a polymer database 102 which includes a plurality of records 104a-n storing information corresponding to a plurality of polymers. Each of the records 104a-n may store information about properties of the corresponding polymer, properties of the corresponding polymer's constituent chemical units, or both. The polymers for which information is stored in the polymer database 102 may be any kind of polymers. For example, the polymers may include polysaccharides, nucleic acids, or polypeptides.

A "polymer" as used herein is a compound having a linear and/or branched backbone of chemical units which are secured together by linkages. In some but not all cases the backbone of the polymer may be branched. The term "backbone" is given its usual meaning in the field of polymer chemistry. The polymers may be heterogeneous in backbone composition thereby containing any possible combination of polymer units linked together such as peptide-nucleic acids. In an embodiment, a polymer is homogeneous in backbone composition and is, for example, a nucleic acid, a polypeptide, a polysaccharide, a carbohydrate, a polyurethane, a polycarbonate, a polyurea, a polyethyleneimine, a polyarylene sulfide, a polysiloxane, a polyimide, a polyacetate, a polyamide, a polyester, or a polythioester. A "polysaccharide" is a biopolymer comprised of linked saccharide or sugar units. A "nucleic acid" as used herein is a biopolymer comprised of nucleotides, such as deoxyribose nucleic acid (DNA) or ribose nucleic acid (RNA). A polypeptide as used herein is a biopolymer comprised of linked amino acids.

As used herein with respect to linked units of a polymer, "linked" or "linkage" means two entities are bound to one another by any physicochemical means. Any linkage known to those of ordinary skill in the art, covalent or non-covalent, is embraced. Such linkages are well known to those of ordinary skill in the art. Natural linkages, which are those ordinarily found in nature connecting the chemical units of a particular polymer, are most common. Natural linkages include, for instance, amide, ester and thioester linkages. The chemical units of a polymer analyzed by the methods of the invention may be linked, however, by synthetic or modified linkages. Polymers where the units are linked by covalent bonds will be most common but also include hydrogen bonded, etc.

The polymer is made up of a plurality of chemical units. A "chemical unit" as used herein is a building block or monomer which can be linked directly or indirectly to other building blocks or monomers to form a polymer. The polymer preferably is a polymer of at least two different linked units. The particular type of unit will depend on the type of polymer. For instance DNA is a biopolymer comprised of a deoxyribose phosphate backbone composed of units of purines and pyrimidines such as adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. RNA is a biopolymer comprised of a ribose phosphate backbone composed of units of purines and pyrimidines such as those described for DNA but wherein uracil is substituted for thymidine. DNA units may be linked to the other units of the polymer by their 5' or 3' hydroxyl group thereby forming an ester linkage. RNA units may be linked to the other units of the polymer by their 5', 3' or 2' hydroxyl group thereby forming an ester linkage. Alternatively, DNA or RNA units having a terminal 5', 3' or 2' amino group may be linked to the other units of the polymer by the amino group thereby forming an amide linkage.

Whenever a nucleic acid is represented by a sequence of letters it will be understood that the nucleotides are in 5'→3' order from left to right and that "A" denotes adenosine, "C" denotes cytidine, "G" denotes guanosine, "T" denotes thymidine, and "U" denotes uracil unless otherwise noted.

The chemical units of a polypeptide are amino acids, including the 20 naturally occurring amino acids as well as modified amino acids. Amino acids may exist as amides or free acids and are linked to the other units in the backbone of the polymers through their a-amino group thereby forming an amide linkage to the polymer.

A polysaccharide is a polymer composed of monosaccharides linked to one another. In many polysaccharides the basic building block of the polysaccharide is actually a disaccharide unit which can be repeating or non-repeating. Thus, a unit when used with respect to a polysaccharide refers to a basic building block of a polysaccharide and can include a monomeric building block (monosaccharide) or a dimeric building block (disaccharide).

A "plurality of chemical units" is at least two units linked to one another.

The polymers may be native or naturally-occurring polymers which occur in nature or non-naturally occurring polymers which do not exist in nature. The polymers typically include at least a portion of a naturally occurring polymer. The polymers can be isolated or synthesized de novo. For example, the polymers can be isolated from natural sources e.g. purified, as by cleavage and gel separation or may be synthesized e.g., (i) amplified in vitro by, for example, polymerase chain reaction (PCR); (ii) synthesized by, for example, chemical synthesis; (iii) recombinantly produced by cloning, etc.

Figure 2A:
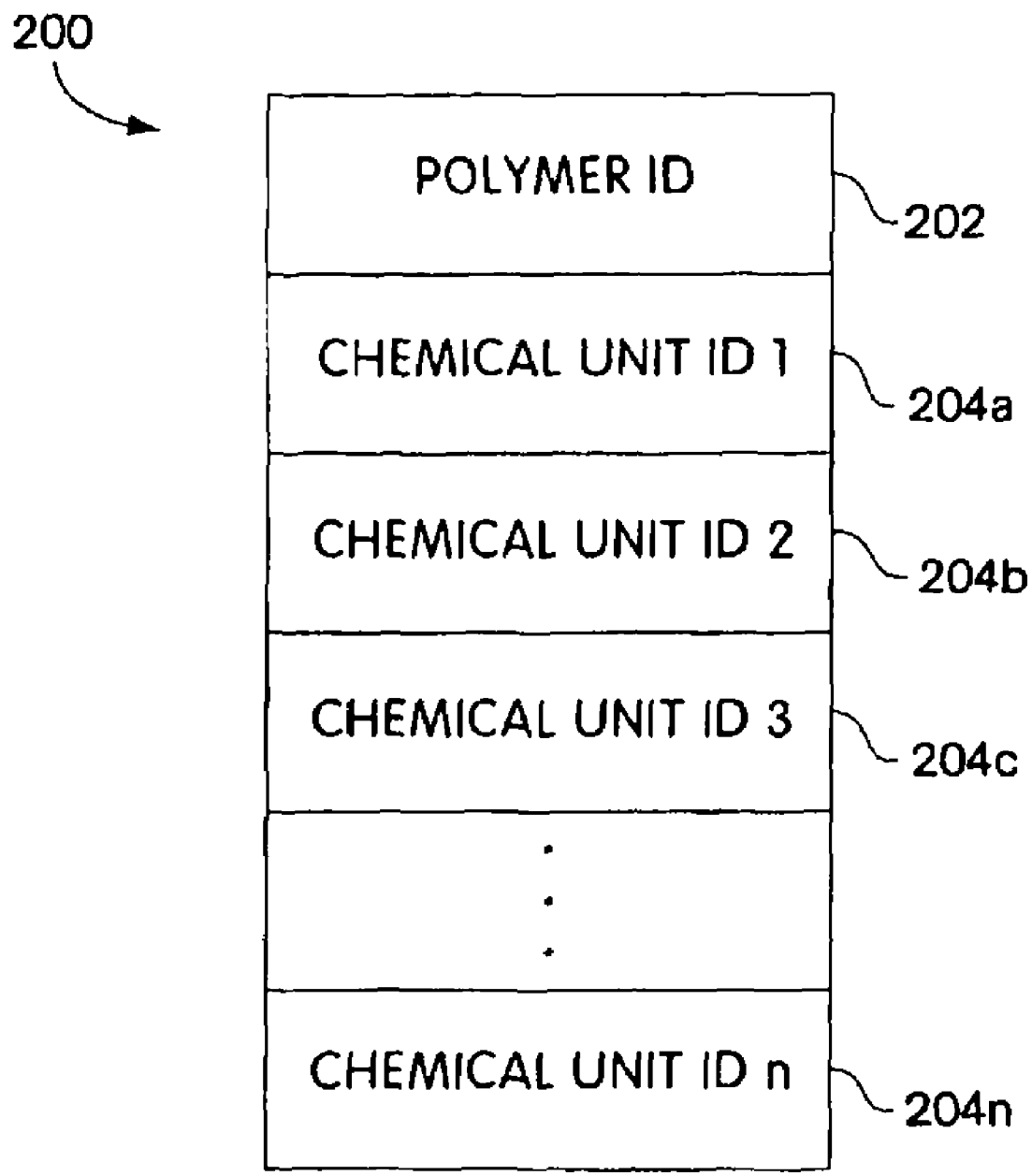
FIG. 2A is a diagram illustrating an example of a record for storing information about a polymer and its constituent chemical units.

FIG. 2A illustrates an example of the format of a data unit 200 in the polymer database 102 (i.e., one of the data units 104a-n). As shown in FIG. 2A, the data unit 200 may include a polymer identifier (ID) 202 that identifies the polymer corresponding to the data unit 200. The polymer ID 202 is described in more detail below with respect to FIG. 2B. The data unit 200 also may include one or more chemical unit identifiers (IDs) 204a-n corresponding to chemical units that are constituents of the polymer corresponding to the data unit 200. The chemical unit IDs 204a-n are described in more detail below with respect to FIG. 2C. The format of the data unit 200 shown in FIG. 2A is merely an example of a format that may be used to represent polymers in the polymer database 102. Polymers may be represented in the polymer database in other ways. For example, the data unit 200 may include only the polymer ID 202 or may only include one or more of the chemical unit IDs 204a-n.

FIG. 2B illustrates an example of the polymer ID 202. The polymer ID 202 may include one or more fields 202a-n for storing information about properties of the polymer corresponding to the data unit 200 (FIG. 2A). Similarly, FIG. 2C illustrates an example of the chemical unit 204a. The chemical unit ID 204a may include one or more fields 206a-m for storing information about properties of the chemical unit corresponding to the chemical unit ID 204a. Although the following description refers to the fields 206a-m of the chemical unit ID 204a, such description is equally applicable to the fields 202a-n of the polymer ID 202a (and the fields of the chemical unit IDs 204b-n).

The fields 206a-m of the chemical unit ID 204a may store any kind of value that is capable of being stored in a computer readable medium, such as, for example, a binary value, a hexadecimal value, an integral decimal value, or a floating point value.

Each field 206a-m may store information about any property of the corresponding chemical unit. A "property" as used herein is a characteristic (e.g., structural characteristic) of the polymer that provides information (e.g., structural information) about the polymer. When the term property is used with respect to any polymer except a polysaccharide the property provides information other than the identity of a unit of the polymer or the polymer itself. A compilation of several properties of a polymer may provide sufficient information to identify a chemical unit or even the entire polymer but the property of the polymer itself does not encompass the chemical basis of the chemical unit or polymer.

When the term property is used with respect to polysaccharides, to define a polysaccharide property, it has the same meaning as described above except that due to the complexity of the polysaccharide, a property may identify a type of monomeric building block of the polysaccharide. Chemical units of polysaccharides are much more complex than chemical units of other polymers, such as nucleic acids and polypeptides. The polysaccharide unit has more variables in addition to its basic chemical structure than other chemical units. For example, the polysaccharide may be acetylated or sulfated at several sites on the chemical unit, or it may be charged or uncharged. Thus, one property of a polysaccharide may be the identity of one or more basic building blocks of the polysaccharides.

A basic building block alone, however, may not provide information about the charge and the nature of substituents of the saccharide or disaccharide. For example, a building block of uronic acid may be iduronic or glucuronic acid. Each of these building blocks may have additional substituents that add complexity to the structure of the chemical unit. A single property, however, may not identify such additional substitutes charges, etc., in addition to identifying a complete building block of a polysaccharide. This information, however, may be assembled from several properties. Thus, a property of a polymer as used herein does not encompass an amino acid or nucleotide but does encompass a saccharide or disaccharide building block of a polysaccharide.

A type of property that provides information about a polymer may depend on a type of polymer being analyzed. For instance, if the polymer is a polysaccharide, properties such as charge, molecular weight, nature and degree of sulfation or acetylation, and type of saccharide may provide information about the polymer. Properties may include, but are not limited to, charge, chirality, nature of substituents, quantity of substituents, molecular weight, molecular length, compositional ratios of substituents or units, type of basic building block of a polysaccharide, hydrophobicity, enzymatic sensitivity, hydrophilicity, secondary structure and conformation (i.e., position of helicies), spatial distribution of substituents, ratio of one set of modifications to another set of modifications (i.e., relative amounts of 2-0 sulfation to N-sulfation or ratio of iduronic acid to glucuronic acid), and binding sites for proteins. Other properties may be identified by those of ordinary skill in the art. A substituent, as used herein is an atom or group of atoms that substitute a unit, but are not themselves the units.

A property of a polymer may be identified by any means known in the art. The procedure used to identify a property may depend on a type of property. Molecular weight, for instance, may be determined by several methods including mass spectrometry. The use of mass spectrometry for determining the molecular weight of polymers is well known in the art. Mass Spectrometry has been used as a powerful tool to characterize polymers because of its accuracy (±1 Dalton) in reporting the masses of fragments generated (e.g., by enzymatic cleavage), and also because only pM sample concentrations are required. For example, matrix-assisted laser desorption ionization mass spectrometry (MALDI-MS) has been described for identifying the molecular weight of polysaccharide fragments in publications such as Rhomberg, A. J. et al, *PNAS, USA*, v. 95, p. 4176-4181 (1998); Rhomberg, A. J. et al, *PNAS, USA*, v. 95, p. 12232-12237 (1998); and Ernst, S. et. al., *PNAS, USA*, v. 95, p. 4182-4187 (1998), each of which is hereby incorporated by reference. Other types of mass spectrometry known in the art, such as, electron spray-MS, fast atom bombardment mass spectrometry (FAB-MS) and collision-activated dissociation mass spectrometry (CAD) can also be used to identify the molecular weight of the polymer or polymer fragments.

The mass spectrometry data may be a valuable tool to ascertain information about the polymer fragment sizes after the polymer has undergone degradation with enzymes or chemicals. After a molecular weight of a polymer is identified, it may be compared to molecular weights of other known polymers. Because masses obtained from the mass spectrometry data are accurate to one Dalton (1 D), a size of one or more polymer fragments obtained by enzymatic digestion may be precisely determined, and a number of substituents (i.e., sulfates and acetates groups present) may be determined. One technique for comparing molecular weights is to generate a mass line and compare the molecular weight of the unknown polymer to the mass line to determine a subpopulation of polymers which have the same molecular weight. A "mass line" as used herein is an information database, preferably in the form of a graph or chart which stores information for each possible type of polymer having a unique sequence based on the molecular weight of the polymer. Thus, a mass line may describe a number of polymers having a particular molecular weight. A two-unit nucleic acid molecule (i.e., a nucleic acid having two chemical units) has 16 (4 units$^2$) possible polymers at a molecular weight corresponding to two nucleotides. A two-unit polysaccharide (i.e., disaccharide) has 32 possible polymers at a molecular weight corresponding to two saccharides. Thus, a mass line may be generated by uniquely assigning a particular mass to a particular length of a given fragment (all possible di, tetra, hexa, octa, up to a hexadecasaccharide), and tabulating the results (An Example is shown in FIG. 4).

Table 1 below shows an example of a computed set of values for a polysaccharide. From Table 1, a number of chemical units of a polymer may be determined from the minimum difference in mass between a fragment of length n+1 and a fragment of length n. For example, if the repeat is a disaccharide unit, a fragment of length n has 2n monosaccharide units. For example, n=1 may correspond to a length of a disaccharide and n=2 may correspond to a length of a tetrasaccharide, etc.

TABLE 1

| Fragment Length n | Minimum difference in mass between n + 1 and n (D) |
|---|---|
| 1 | 101.13 |
| 2 | 13.03 |
| 3 | 13.03 |
| 4 | 9.01 |
| 5 | 9.01 |
| 6 | 4.99 |
| 7 | 4.99 |
| 8 | 0.97 |
| 9 | 0.97 |

Because mass spectrometry data indicates the mass of a fragment to 1D accuracy, a length may be assigned uniquely to fragment by looking up a mass on the mass line. Further, it may be determined from the mass line that, within a fragment of particular length higher than a disaccharide, there is a minimum of 4.02 D different in masses indicating that two acetate groups (84.08 D) replaced a sulfate group (80.06 D). Therefore, a number of sulfates and acetates of a polymer fragment may be determined from the mass from the mass spectrometry data and, such number may be assigned to the polymer fragment.

In addition to molecular weight, other properties may be determined using methods known in the art. The compositional ratios of substituents or chemical units (quantity and type of total substituents or chemical units) may be determined using methodology known in the art, such as capillary electrophoresis. A polymer may be subjected to an experimental constraint such as enzymatic or chemical degradation to separate each of the chemical units of the polymers. These units then may be separated using capillary electrophoresis to determine the quantity and type of substituents or chemical units present in the polymer. Additionally, a number of substituents or chemical units can be determined using calculations based on the molecular weight of the polymer.

In the method of capillary gel-electrophoresis, reaction samples may be analyzed by small-diameter, gel-filled capillaries. The small diameter of the capillaries (50 µm) allows for efficient dissipation of heat generated during electrophoresis. Thus, high field strengths can be used without excessive Joule heating (400 V/m), lowering the separation time to about 20 minutes per reaction run, therefor increasing resolution over conventional gel electrophoresis. Additionally, many capillaries may be analyzed in parallel, allowing amplification of generated polymer information.

In addition to being useful for identifying a property, compositional analysis also may be used to determine a presence and composition of an impurity as well as a main property of the polymer. Such determinations may be accomplished if the impurity does not contain an identical composition as the polymer. To determine whether an impurity is present may involve accurately integrating an area under each peak that appears in the electrophoretogram and normalizing the peaks to the smallest of the major peaks. The sum of the normalized peaks should be equal to one or close to being equal to one. If it is not, then one or more impurities are present. Impurities even may be detected in unknown samples if at least one of the disaccharide units of the impurity differs from any disaccharide unit of the unknown.

If an impurity is present, one or more aspects of a composition of the components may be determined using capillary electrophoresis. Because all known disaccharide units may be baseline-separated by the capillary electrophoresis method described above and because migration times typically are determined using electrophoresis (i.e., as opposed to electroosmotic flow) and are reproducible, reliable assignment to a polymer fragment of the various saccharide units may be achieved. Consequently, both a composition of the major peak and a composition of a minor contaminant may be assigned to a polymer fragment. The composition for both the major and minor components of a solution may be assigned as described below.

One example of such assignment of compositions involves determining the composition of the major AT-III binding HLGAG decasaccharide (+DDD4−7) and its minor contaminant (+D5D4−7) present in solution in a 9:1 ratio. Complete digestion of this 9:1 mixture with a heparinases yields 4 peaks: three representative of the major decasaccharide (viz., D, 4, and −7) which are also present in the contaminant and one peak, 5, that is present only in the contaminant. In other words, the area of each peak for D, 4, and −7 represents an additive combination of a contribution from the major decasaccharide and the contribution from the contaminant, whereas the peak for 5 represents only the contaminant.

To assign the composition of the contaminant and the major component, the area under the 5 peak may be used as a starting point. This area represents an area under the peak for one disaccharide unit of the contaminant. Subtracting this area from the total area of 4 and −7 and subtracted twice this area from an area under D yields a 1:1:3 ratio of 4:−7:D. Such a ratio confirms the composition of the major component and indicates that the composition of the impurity is two Ds, one 4, one −7 and one 5.

Methods of identifying other types of properties may be easily identifiable to those of skill in the art and may depend on the type of property and the type of polymer. For example, hydrophobicity may be determined using reverse-phase high-pressure liquid chromatography (RP-HPLC). Enzymatic sensitivity may be identified by exposing the polymer to an enzyme and determining a number of fragments present after such exposure. The chirality may be determined using circular dichroism. Protein binding sites may be determined by mass spectrometry, isothermal calorimetry and NMR. Enzymatic modification (not degradation) may be determined in a similar manner as enzymatic degradation, i.e., by exposing a substrate to the enzyme and using MALDI-MS to determine if the substrate is modified. For example, a sulfotransferase may transfer a sulfate group to an HS chain having a concomitant increase in 80 Da. Conformation may be determined by modeling and nuclear magnetic resonance (NMR). The relative amounts of sulfation may be determined by compositional analysis or approximately determined by raman spectroscopy.

Figure 2D:
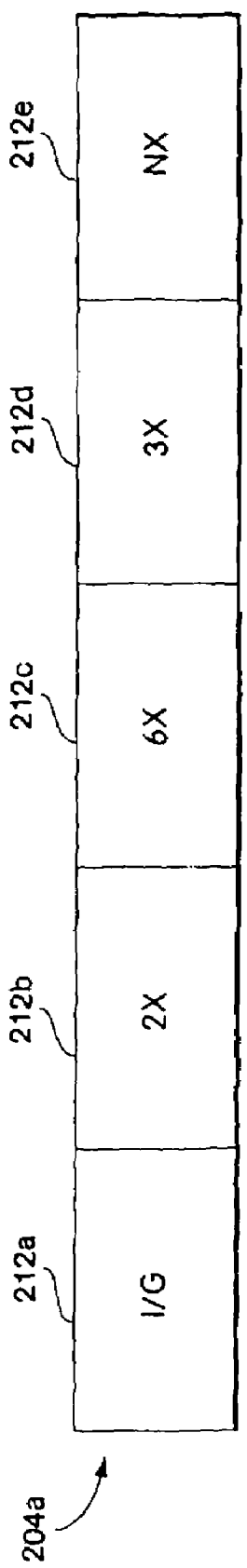
FIG. 2B is a diagram illustrating an example of a record for storing information about a polymer.
FIG. 2C is a diagram illustrating an example of a record for storing information about constituent chemical units of a polymer.

FIG. 2D illustrates an example of the chemical unit ID 204a. The chemical unit ID 204a contains one or more fields 212a-e for storing information about properties of a heparin-like glycosaminoglycan (HLGAG). HLGAGs are complex polysaccharide molecules made up of disaccharide repeat units comprising hexoseamine and glucuronic/iduronic acid that are linked by α/β1-4 glycosidic linkages. These defining units may be modified by: sulfation at the N, 3-O and 6-O position of the hexoseamine, 2-O sulfation of the uronic acid, and C5 epimerization that converts the glucuronic acid to iduronic acid. The disaccharide unit of HLGAG may be represented as:

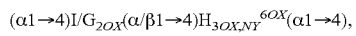

$(\alpha 1 \rightarrow 4) I/G_{2OX}(\alpha/\beta 1 \rightarrow 4) H_{3OX,NY}{}^{6OX}(\alpha 1 \rightarrow 4),$ where X may be sulfated (—SO$_3$H) or unsulfated (—H), and Y may be sulfated (—SO$_3$H) or acetylated (—COCH$_3$) or, in rare cases, neither sulfated nor acetylated.

The fields 212a-e may store any kinds of values, such as, for example single-bit values, single-digit hexadecimal values, or decimal values. In one embodiment, the chemical unit ID 204a includes each of the following fields: (1) a field 212a for storing a value indicating whether the polymer contains an iduronic or a glucuronic acid (I/G); (2) a field 212b for storing a value indicating whether the 2X position of the iduronic or glucuronic acid is sulfated or unsulfated; (3) a field 212c for storing a value indicating whether the hexoseamine is sulfated or unsulfated; (4) a field 212d indicating whether the 3X position of the hexoseamine is sulfated or unsulfated; and (5) a field 212e indicating whether the NX position of the hexoseamine is sulfated or acetylated. Optionally, each of the fields 212a-e may be represented as a single bit.

Table 2 illustrates an example of a data structure having a plurality of entries, where each entry represents an HLGAG encoded in accordance with FIG. 2D. Bit values for each of the fields 212a-e may be assigned in any known manner. For example, with respect to field 212a (I/G), a value of one may indicate Iduronic and a value of zero may indicate Glucuronic, or vice versa.

TABLE 2

| I/G | 2X | 6X | 3X | NX | ALPH CODE | DISACC | MASS (AU) |
|---|---|---|---|---|---|---|---|
| 0 | 0 | 0 | 0 | 0 | 0 | I-H$_{NAc}$ | 379.33 |
| 0 | 0 | 0 | 0 | 1 | 1 | I-H$_{NS}$ | 417.35 |
| 0 | 0 | 0 | 1 | 0 | 2 | I-H$_{NAc,3S}$ | 459.39 |
| 0 | 0 | 0 | 1 | 1 | 3 | I-H$_{NS,3S}$ | 497.41 |
| 0 | 0 | 1 | 0 | 0 | 4 | I-H$_{NAc,6S}$ | 459.39 |
| 0 | 0 | 1 | 0 | 1 | 5 | I-H$_{NS,6S}$ | 497.41 |
| 0 | 0 | 1 | 1 | 0 | 6 | I-H$_{NAc,3S,6S}$ | 539.45 |
| 0 | 0 | 1 | 1 | 1 | 7 | I-H$_{NS,3S,6S}$ | 577.47 |
| 0 | 1 | 0 | 0 | 0 | 8 | I$_{2S}$-H$_{NAc}$ | 459.39 |
| 0 | 1 | 0 | 0 | 1 | 9 | I$_{2S}$-H$_{NS}$ | 497.41 |
| 0 | 1 | 0 | 1 | 0 | A | I$_{2S}$-H$_{NAc,3S}$ | 539.45 |
| 0 | 1 | 0 | 1 | 1 | B | I$_{2S}$-H$_{NS,3S}$ | 577.47 |
| 0 | 1 | 1 | 0 | 0 | C | I$_{2S}$-H$_{NAc,6S}$ | 539.45 |
| 0 | 1 | 1 | 0 | 1 | D | I$_{2S}$-H$_{NS,6S}$ | 577.47 |
| 0 | 1 | 1 | 1 | 0 | E | I$_{2S}$-H$_{NAc,3S,6S}$ | 619.51 |
| 0 | 1 | 1 | 1 | 1 | F | I$_{2S}$-H$_{NS,3S,6S}$ | 657.53 |
| 1 | 0 | 0 | 0 | 0 | −0 | G-H$_{NAc}$ | 379.33 |
| 1 | 0 | 0 | 0 | 1 | −1 | G-H$_{NS}$ | 417.35 |
| 1 | 0 | 0 | 1 | 0 | −2 | G-H$_{NAc,3S}$ | 459.39 |
| 1 | 0 | 0 | 1 | 1 | −3 | G-H$_{NS,3S}$ | 497.41 |
| 1 | 0 | 1 | 0 | 0 | −4 | G-H$_{NAc,6S}$ | 459.39 |
| 1 | 0 | 1 | 0 | 1 | −5 | G-H$_{NS,6S}$ | 497.41 |
| 1 | 0 | 1 | 1 | 0 | −6 | G-H$_{NAc,3S,6S}$ | 539.45 |
| 1 | 0 | 1 | 1 | 1 | −7 | G-H$_{NS,3S,6S}$ | 577.47 |
| 1 | 1 | 0 | 0 | 0 | −8 | G$_{2S}$-H$_{NAc}$ | 459.39 |
| 1 | 1 | 0 | 0 | 1 | −9 | G$_{2S}$-H$_{NS}$ | 497.41 |
| 1 | 1 | 0 | 1 | 0 | −A | G$_{2S}$-H$_{NAc,3S}$ | 539.45 |
| 1 | 1 | 0 | 1 | 1 | −B | G$_{2S}$-H$_{NS,3S}$ | 577.47 |
| 1 | 1 | 1 | 0 | 0 |  | G$_{2S}$-H$_{NAc,6S}$ |  |
| 1 | 1 | 1 | 0 | 1 | −D | G$_{2S}$-H$_{NS,6S}$ | 577.47 |
| 1 | 1 | 1 | 1 | 0 | −E | G$_{2S}$-H$_{NAc,3S,6S}$ | 619.51 |
| 1 | 1 | 1 | 1 | 1 | −F | G$_{2S}$-H$_{NS,3S,6S}$ | 657.53 |

Representing a HLGAG using a bit field may have a number of advantages. Because a property of an HLGAG may have one of two possible states, a binary bit is ideally-suited for storing information representing an HLGAG property. Bit fields may be used to store such information in a computer readable medium (e.g., a computer memory or storage device), for example, by packing multiple bits (representing multiple fields) into a single byte or sequence of bytes. Furthermore, bit fields may be stored and manipulated quickly and efficiently by digital computer processors, which typically store information using bits and which typically can quickly perform operations (e.g., shift, AND, OR) on bits. For example, as described in more detail below, a plurality of properties each stored as a bit field can be searched more quickly than searches conducted using typical character-based searching methods.

Further, using bit fields to represent properties of HLGAGs permits a user to more easily incorporate additional properties (e.g., 4-0 sulfation vs. unsulfation) into a chemical unit ID 204a by adding extra bits to represent the additional properties.

In one embodiment, the four fields 212b-e (each of which may store a single-bit value) may be represented as a single hexadecimal (base 16) number where each of the fields 212a-e represents one bit of the hexadecimal number. Using hexadecimal numbers to represent disaccharide units is convenient both for representation and processing because hexadecimal digits are a common form of representation used by conventional computers.

Optionally, the five fields 212a-e of the record 210 may be represented as signed hexadecimal digit, in which the fields 212b-212e collectively encode a single-digit hexadecimal number as described above and the I/G field is used as a sign bit. In such a signed representation, the hexadecimal numbers 0-F may be used to code chemical units containing iduronic acid and the hexadecimal numbers −0 to −F may be used to code units containing glucuronic acid. The chemical unit ID 204a may, however, be encoded using other forms of representations, such as by using a twos-complement representation.

The fields 212a-e of the chemical unit ID 204a may be arranged in any order. For example, a gray code system may be used to code HLGAGs. In a gray code numbering scheme, each successive value differs from the previous value only in a single bit position. For example, in the case of HLGAGs, the values representing HLGAGs may be arranged so that any two neighboring values differ in the value of only one property. An example of a gray code system used to code HLGAGs is shown in Table 3.

TABLE 3

| I/G 16 | 2X 8 | 6X 4 | 3X 2 | NX 1 | Numeric Value | DISACC | MASS (ΔU) |
|---|---|---|---|---|---|---|---|
| 0 | 0 | 0 | 0 | 0 | 0 | I-$H_{NAc}$ | 379.33 |
| 0 | 0 | 0 | 0 | 1 | 1 | I-$H_{NS}$ | 417.35 |
| 0 | 0 | 0 | 1 | 1 | 3 | I-$H_{NS,3S}$ | 497.41 |
| 0 | 0 | 0 | 1 | 0 | 2 | I-$H_{NAc,3S}$ | 459.39 |
| 0 | 0 | 1 | 1 | 0 | 6 | I-$H_{NAc,3S,6S}$ | 539.45 |
| 0 | 0 | 1 | 1 | 1 | 7 | I-$H_{NS,3S,6S}$ | 577.47 |
| 0 | 0 | 1 | 0 | 1 | 5 | I-$H_{NS,6S}$ | 497.41 |
| 0 | 0 | 1 | 0 | 0 | 4 | I-$H_{NAc,6S}$ | 459.39 |
| 0 | 1 | 1 | 0 | 0 | 12 | $I_{2S}$-$H_{NAc,6S}$ | 539.45 |
| 0 | 1 | 1 | 0 | 1 | 13 | $I_{2S}$-$H_{NS,6S}$ | 577.47 |
| 0 | 1 | 1 | 1 | 1 | 15 | $I_{2S}$-$H_{NS,3S,6S}$ | 657.53 |
| 0 | 1 | 1 | 1 | 0 | 14 | $I_{2S}$-$H_{NAc,3S,6S}$ | 619.51 |
| 0 | 1 | 0 | 1 | 0 | 10 | $I_{2S}$-$H_{NAc,3S}$ | 539.45 |
| 0 | 1 | 0 | 1 | 1 | 11 | $I_{2S}$-$H_{NS,3S}$ | 577.47 |
| 0 | 1 | 0 | 0 | 1 | 9 | $I_{2S}$-$H_{NS}$ | 497.41 |
| 0 | 1 | 0 | 0 | 0 | 8 | $I_{2S}$-$H_{NAc}$ | 459.39 |
| 1 | 1 | 0 | 0 | 0 | 24 | $G_{2S}$-$H_{NAc}$ | 459.39 |
| 1 | 1 | 0 | 0 | 1 | 25 | $G_{2S}$-$H_{NS}$ | 497.41 |
| 1 | 1 | 0 | 1 | 1 | 27 | $G_{2S}$-$H_{NS,3S}$ | 577.41 |
| 1 | 1 | 0 | 1 | 0 | 26 | $G_{2S}$-$H_{NAc,3S}$ | 539.45 |
| 1 | 1 | 1 | 1 | 0 | 30 | $G_{2S}$-$H_{NAc,3S,6S}$ | 619.51 |
| 1 | 1 | 1 | 1 | 1 | 31 | $G_{2S}$-$H_{NS,3S,6S}$ | 657.53 |
| 1 | 1 | 1 | 0 | 1 | 29 | $G_{2S}$-$H_{NS,6S}$ | 577.47 |
| 1 | 1 | 1 | 0 | 0 | 28 | $G_{2S}$-$H_{NAc,6S}$ | 539.45 |
| 1 | 0 | 1 | 0 | 0 | 20 | G-$H_{NAc,6S}$ | 459.39 |
| 1 | 0 | 1 | 0 | 1 | 21 | G-$H_{NS,6S}$ | 497.41 |
| 1 | 0 | 1 | 1 | 1 | 23 | G-$H_{NS,3S,6S}$ | 577.47 |
| 1 | 0 | 1 | 1 | 0 | 22 | G-$H_{NAc,3S,6S}$ | 539.45 |
| 1 | 0 | 0 | 1 | 0 | 18 | G-$H_{NAc,3S}$ | 459.39 |
| 1 | 0 | 0 | 1 | 1 | 19 | G-$H_{NS,3S}$ | 497.41 |
| 1 | 0 | 0 | 0 | 1 | 17 | G-$H_{NS}$ | 417.35 |
| 1 | 0 | 0 | 0 | 0 | 16 | G-$H_{NAc}$ | 379.33 |

Table 3 illustrates that use of a gray coding scheme arranges the disaccharide building blocks such that neighboring table entries differ from each other only in the value of a single property. One advantage of using gray codes to encode HLGAGs is that a biosynthesis of HLGAG fragments may follow a specific sequence of modifications starting from the basic building block G-$H_{HNac}$.

In Table 3, bit weights of 8, 4, 2, and 1 are used to calculate the numerical equivalent of a hexadecimal number with the most significant bit (I/G) being used as a sign bit. For example, the hexadecimal code A (01010 binary) is equal to 8*1+4*0+2*1+1*0=10.

In another embodiment, the weights of each of the fields 212a-e may be changed thereby implementing an alternative weighting system. For example, bit fields 212a-e may have weights of 16, 8, 4, −2, and −1, respectively, as shown in Table 4.

TABLE 4

| I/G 16 | 2X 8 | NX 4 | 3X −2 | 6X −1 | Value | DISACC | MASS (ΔU) |
|---|---|---|---|---|---|---|---|
| 0 | 0 | 0 | 0 | 0 | 0 | I-$H_{NAc}$ | 379.33 |
| 0 | 0 | 0 | 0 | 1 | −1 | I-$H_{NAc,6S}$ | 459.39 |
| 0 | 0 | 0 | 1 | 0 | −2 | I-$H_{NAc,3S}$ | 459.39 |
| 0 | 0 | 0 | 1 | 1 | −3 | I-$H_{NAc,3S,6S}$ | 539.45 |
| 0 | 0 | 1 | 0 | 0 | 4 | I-$H_{NS}$ | 417.35 |
| 0 | 0 | 1 | 0 | 1 | 3 | I-$H_{NS,6S}$ | 497.41 |
| 0 | 0 | 1 | 1 | 0 | 2 | I-$H_{NS,3S}$ | 497.41 |
| 0 | 0 | 1 | 1 | 1 | 1 | I-$H_{NS,3S,6S}$ | 577.47 |
| 0 | 1 | 0 | 0 | 0 | 8 | $I_{2S}$-$H_{NAc}$ | 459.39 |
| 0 | 1 | 0 | 0 | 1 | 7 | $I_{2S}$-$H_{NAc,6S}$ | 539.45 |
| 0 | 1 | 0 | 1 | 0 | 6 | $I_{2S}$-$H_{NAc,3S}$ | 539.45 |
| 0 | 1 | 0 | 1 | 1 | 5 | $I_{2S}$-$H_{NAc,3S,6S}$ | 619.51 |
| 0 | 1 | 1 | 0 | 0 | 12 | $I_{2S}$-$H_{NS}$ | 497.41 |
| 0 | 1 | 1 | 0 | 1 | 11 | $I_{2S}$-$H_{NS,6S}$ | 577.47 |
| 0 | 1 | 1 | 1 | 0 | 10 | $I_{2S}$-$H_{NS,3S}$ | 577.47 |
| 0 | 1 | 1 | 1 | 1 | 9 | $I_{2S}$-$H_{NS,3S,6S}$ | 657.53 |
| 1 | 0 | 0 | 0 | 0 | 16 | G-$H_{NAc}$ | 379.33 |
| 1 | 0 | 0 | 0 | 1 | 15 | G-$H_{NAc,6S}$ | 459.39 |
| 1 | 0 | 0 | 1 | 0 | 14 | G-$H_{NAc,3S}$ | 459.39 |
| 1 | 0 | 0 | 1 | 1 | 13 | G-$H_{NAc,3S,6S}$ | 539.45 |
| 1 | 0 | 1 | 0 | 0 | 20 | G-$H_{NS}$ | 417.35 |
| 1 | 0 | 1 | 0 | 1 | 19 | G-$H_{NS,6S}$ | 497.41 |
| 1 | 0 | 1 | 1 | 0 | 18 | G-$H_{NS,3S}$ | 497.41 |
| 1 | 0 | 1 | 1 | 1 | 17 | G-$H_{NS,3S,6S}$ | 577.47 |
| 1 | 1 | 0 | 0 | 0 | 24 | $G_{2S}$-$H_{NAc}$ | 459.39 |
| 1 | 1 | 0 | 0 | 1 | 23 | $G_{2S}$-$H_{NAc,6S}$ | 539.45 |
| 1 | 1 | 0 | 1 | 0 | 22 | $G_{2S}$-$H_{NAc,3S}$ | 539.45 |
| 1 | 1 | 0 | 1 | 1 | 21 | $G_{2S}$-$H_{NAc,3S,6S}$ | 619.51 |
| 1 | 1 | 1 | 0 | 0 | 28 | $G_{2S}$-$H_{NS}$ | 497.41 |
| 1 | 1 | 1 | 0 | 1 | 27 | $G_{2S}$-$H_{NS,6S}$ | 577.47 |
| 1 | 1 | 1 | 1 | 0 | 26 | $G_{2S}$-$H_{NS,3S}$ | 577.47 |
| 1 | 1 | 1 | 1 | 1 | 25 | $G_{2S}$-$H_{NS,3S,6S}$ | 657.53 |

Modifying the weights of the bits may be used to score the disaccharide units. For example, a database of sequences may be created and the different disaccharide units may be scored based on their relative abundance in the sequences present in the database. Some units, for example, I-$H_{NAc,3S}^{6S}$, which rarely occur in naturally-occurring HLGAGs, may receive a low score based on a scheme in which the bits are weighted in the manner shown in Table 4.

Optionally, the sulfation and acetylation positions may be arranged in an shown in Table 2: I/G, 2X, 6X, 3X, NX. These positions may, however, be arranged differently, resulting in a same set of codes representing different disaccharide units. Table 5, for example, shows an arrangement in which the positions are arranged as I/G, 2X, NX, 3X, 6X.

TABLE 5

| I/G | 2X | NX | 3X | 6X | ALPH CODE | DISACC | MASS (ΔU) |
|---|---|---|---|---|---|---|---|
| 0 | 0 | 0 | 0 | 0 | 0 | I-$H_{NAc}$ | 379.33 |
| 0 | 0 | 0 | 0 | 1 | 1 | I-$H_{NAc,6S}$ | 459.39 |
| 0 | 0 | 0 | 1 | 0 | 2 | I-$H_{NAc,3S}$ | 459.39 |
| 0 | 0 | 0 | 1 | 1 | 3 | I-$H_{NAc,3S,6S}$ | 539.45 |
| 0 | 0 | 1 | 0 | 0 | 4 | I-$H_{NS}$ | 417.35 |
| 0 | 0 | 1 | 0 | 1 | 5 | I-$H_{NS,6S}$ | 497.41 |
| 0 | 0 | 1 | 1 | 0 | 6 | I-$H_{NS,3S}$ | 497.41 |
| 0 | 0 | 1 | 1 | 1 | 7 | I-$H_{NS,3S,6S}$ | 577.47 |

TABLE 5-continued

| I/G | 2X | NX | 3X | 6X | ALPH CODE | DISACC | MASS (ΔU) |
|---|---|---|---|---|---|---|---|
| 0 | 1 | 0 | 0 | 0 | 8 | $I_{2S}$-$H_{NAc}$ | 459.39 |
| 0 | 1 | 0 | 0 | 1 | 9 | $I_{2S}$-$H_{NAc,6S}$ | 539.45 |
| 0 | 1 | 0 | 1 | 0 | A | $I_{2S}$-$H_{NAc,3S}$ | 539.45 |
| 0 | 1 | 0 | 1 | 1 | B | $I_{2S}$-$H_{NAc,3S,6S}$ | 619.51 |
| 0 | 1 | 1 | 0 | 0 | C | $I_{2S}$-$H_{NS}$ | 497.41 |
| 0 | 1 | 1 | 0 | 1 | D | $I_{2S}$-$H_{NS,6S}$ | 577.47 |
| 0 | 1 | 1 | 1 | 0 | E | $I_{2S}$-$H_{NS,3S}$ | 577.47 |
| 0 | 1 | 1 | 1 | 1 | F | $I_{2S}$-$H_{NS,3S,6S}$ | 657.53 |
| 1 | 0 | 0 | 0 | 0 | -0 | G-$H_{NAc}$ | 379.33 |
| 1 | 0 | 0 | 0 | 1 | -1 | G-$H_{NAc,6S}$ | 459.39 |
| 1 | 0 | 0 | 1 | 0 | -2 | G-$H_{NAc,3S}$ | 459.39 |
| 1 | 0 | 0 | 1 | 1 | -3 | G-$H_{NAc,3S,6S}$ | 539.45 |
| 1 | 0 | 1 | 0 | 0 | -4 | G-$H_{NS}$ | 417.35 |
| 1 | 0 | 1 | 0 | 1 | -5 | G-$H_{NS,6S}$ | 497.41 |
| 1 | 0 | 1 | 1 | 0 | -6 | G-$H_{NS,3S}$ | 497.41 |
| 1 | 0 | 1 | 1 | 1 | -7 | G-$H_{NS,3S,6S}$ | 577.47 |
| 1 | 1 | 0 | 0 | 0 | -8 | $G_{2S}$-$H_{NAc}$ | 459.39 |
| 1 | 1 | 0 | 0 | 1 | -9 | $G_{2S}$-$H_{NAc,6S}$ | 539.45 |
| 1 | 1 | 0 | 1 | 0 | -A | $G_{2S}$-$H_{NAc,3S}$ | 539.45 |
| 1 | 1 | 0 | 1 | 1 | -B | $G_{2S}$-$H_{NAc,3S,6S}$ | 619.51 |
| 1 | 1 | 1 | 0 | 0 | -C | $G_{2S}$-$H_{NS}$ | 497.41 |
| 1 | 1 | 1 | 0 | 1 | -D | $G_{2S}$-$H_{NS,6S}$ | 577.47 |
| 1 | 1 | 1 | 1 | 0 | -E | $G_{2S}$-$H_{NS,3S}$ | 577.47 |
| 1 | 1 | 1 | 1 | 1 | -F | $G_{2S}$-$H_{NS,3S,6S}$ | 657.53 |

It has been observed that disaccharide units in some HLGAG sequences are neither N-sulfated nor N-acetylated. Such disaccharide units may be represented using the chemical unit ID 204a in any of a number of ways.

If the properties of a chemical unit are represented by bit fields, disaccharide units that contain a free amine in the N position may be represented by, for example, adding an additional bit field. For example, referring to FIG. 2D, an additional field NY may be used in the chemical unit ID 204a. For example, an NY field having a value of zero may correspond to a free amine, and an NY field having a value of one may correspond to N-acetylation, or vice versa. Further, a value of one in the NX field 212e may correspond to N-sulfation.

Optionally, disaccharide units that contain a free amine in the N position may be represented using a tristate field. For example, the field 212e (NX) in the chemical unit ID 204a may be a tristate field having three permissible values. For example, a value of zero may correspond to a free amine, a value of one may correspond to N-acetylation, and a value of two could correspond to N-sulfation. Similarly, the values of any of the fields 212a-e may be represented using a number system with a base higher than two. For example, if the value of the field 212e (NX) is represented by a single-digit number having a base of three, then the field 212e may store three permissible values.

Referring to FIG. 1, user may perform a query on the polymer database 102 to search for particular information. For example, a user may search the polymer database 102 for specified polymers, specified chemical units, or polymers or chemical units having specified properties. A user may provide to a query user interface 108 user input 106 indicating properties for which to search. The user input 106 may, for example, indicate one or more chemical units, a polymer of chemical units or one or more properties to search for using, for example, a standard character-based notation. The query user interface 108 may, for example, provide a graphical user interface (GUI) which allows the user to select from a list of properties using an input device such as a keyboard or a mouse.

The query user interface 108 may generate a search query 110 based on the user input 106. A search engine 112 may receive the search query 110 and generate a mask 114 based on the search query. Example formats of the mask 114, and example techniques to determine whether properties specified by the mask 114 match properties of polymers in the polymer database 102 are described in more detail below in connection to FIG. 3.

The search engine 112 may determine whether properties specified by the mask 114 match properties of polymers stored in the polymer database 102. Subsequently, the search engine 112 may generate search results 116 based on the search indicating whether the polymer database 102 includes polymers having the properties specified by the mask 114. The search results 116 also may indicate polymers in the polymer database 102 that have the properties specified by the mask 114. For example, if the user input 106 specified properties of a chemical unit, the search results 116 may indicate which polymers in the polymer database 102 include the specified chemical unit. Alternatively, if the user input 106 specified particular chemical unit properties, the search results 116 may indicate polymers in the polymer database 102 that include chemical units having the specified chemical unit properties. Similarly, if the user input 106 specified particular polymer properties, the search results 116 may indicate which polymers in the polymer database 102 have the specified polymer properties.

Figure 3:
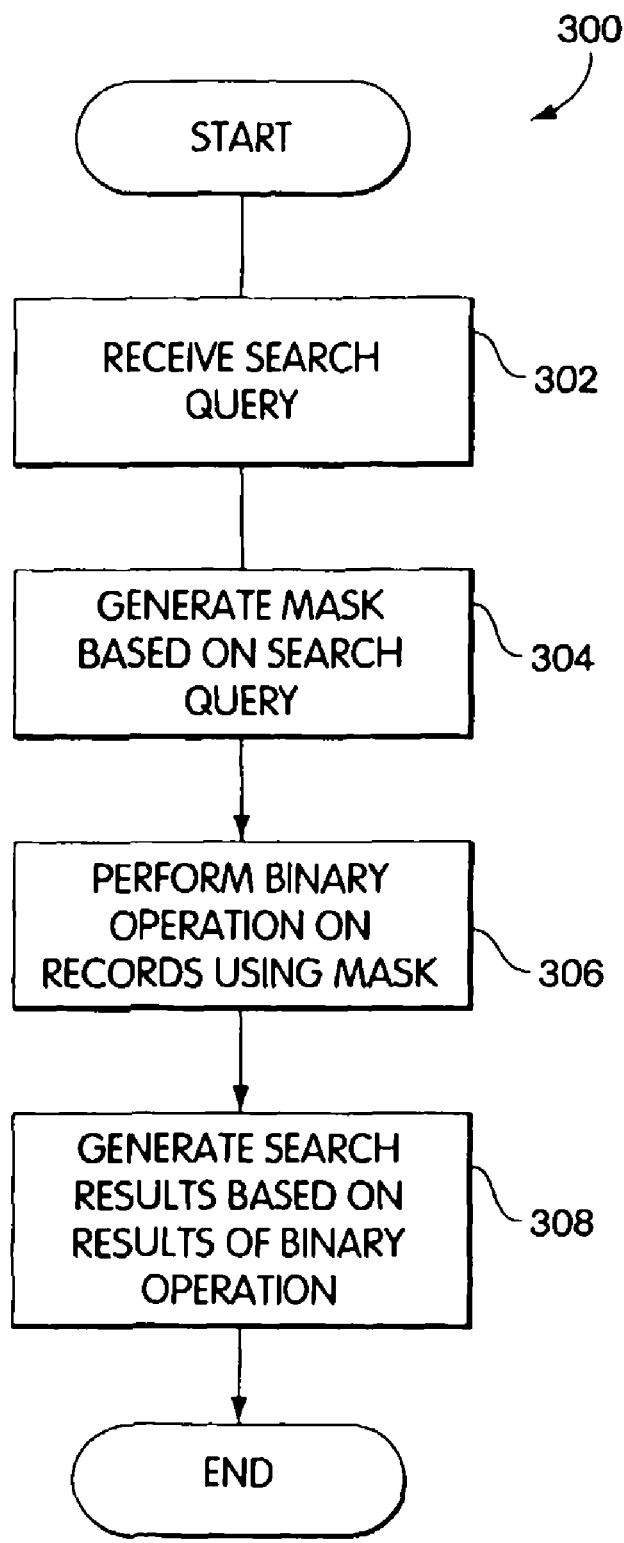
FIG. 3 is a flow chart illustrating an example of a method for determining whether properties of a first polymer of chemical units match properties of a second chemical unit.

FIG. 3 is a flowchart illustrating an example of a process 300 that may be used by the search engine 112 to generate the search results 116. In act 302, the search engine 112 may receive a search query 110 from the query user interface 108. Next, in act 304, the search engine 112 may generate a mask 114 generated based on the search query 110. In a following act 306, the search engine 112 may perform a binary operation on one or more of the records 104a-n in the polymer database 102 by applying the mask 114. Next, in act 308, the search engine 112 may generate the search results 116 based on the results of the binary operation performed in step 306.

The process 300 will now be described in more detail with respect to an embodiment in which the fields 206a-m of the chemical unit 204a are binary fields. In act 302, the received search query 110 may indicate to search the polymer database 102 for a particular chemical unit, e.g. the chemical unit $I_{2S}$-$H_{NS}$. If, for example, the coding scheme shown in Table 1 is used to encode chemical units in the polymer database, the chemical unit $I_{2S}$-$H_{NS}$ may be represented by a binary value of 01001. To generate the mask 114 for this chemical unit (step 304), the search engine 112 may use the binary value of the chemical unit, i.e., 01001, as the value of the mask 114. As a result, the values of the bits of the mask 114 may specify the properties of the chemical unit $I_{2S}$-$H_{NS}$. For example, the value of zero in the leftmost bit position may indicate Iduronic, and the value of one in the next bit position may indicate that the 2X position is sulfated.

The search engine 112 may use this mask 114 to determine whether polymers in the polymer database 102 contain the chemical unit $I_{2S}$-$H_{NS}$. To make this determination, the search engine 112 may perform a binary operation on the data units 104a-n of the polymer database 102 using the mask 114 (step 306). For example, the search engine 112 may perform a logical AND operation on each chemical unit of each of the polymers in the polymer database 102 using the mask 114. If the result of the logical AND operation on a particular chemical unit is equal to the value of the mask 114, then the chemical unit may satisfy the search query 110, and, in act 308, the search engine 112 may indicate a successful match in the search results 116. The search engine 112 may generate additional information in the search results 116, such as the polymer identifier of the polymer containing the matching chemical unit.

In response to receiving the search query in act 302, in act 304, the search engine 112 also may generate the mask 114 that indicates one or more properties of a particular polymer or chemical unit. To generate the mask 114 for such a search query, the search engine 112 may set each bit position in the mask according to a property specified by the search query to the value specified by the search query. Consider, for example, search query 110 that indicates a search for all chemical units in which both the 2X position and the 6X position are sulfated. To generate a mask corresponding to this search query, the search engine 112 may set the bit positions of the mask corresponding to the 2X and 6X positions to a value corresponding to being sulfated. Using the coding scheme shown above in Table 1, for example, in which the 2X and 6X positions have bit positions of 3 and 2 (counting from the rightmost position beginning at bit position zero), respectively, the mask corresponding to this search query is 01100. The two bits of this mask that have a value of one correspond to the bit positions in Table 1 corresponding to the 2X and 6X positions.

To determine whether the one or more properties of a particular chemical unit in the polymer database 102 match the one or more properties specified by the mask 114, the search engine 112 may perform a logical AND operation on the chemical unit identifier of the chemical unit in the polymer database 102 using the mask 114. To generate search results for this chemical unit (i.e., act 308), the search engine 112 may compare the result of the logical AND operation to the mask 114. If the values of the bit positions of the logical AND operation corresponding to the properties specified by the search query are equal to the values of the same bit positions of the mask 114, then the chemical unit has the properties specified by the search query 110, and the search engine 112 indicates a successful match in the search results 116.

For example, consider the search query 110 described above, which indicates a search for all chemical units in which both the 2X position and the 6X position are sulfated. Using the coding scheme of Table 1, the bit positions corresponding to the 2X and 6X positions are bit positions 3 and 2. Therefore, after performing a logical AND operation on the chemical unit identifier of a chemical unit using the mask 114, the search engine 112 compares bit positions 3 and 2 of the result of the logical AND operation to bit positions 3 and 2 of the mask. If the values in both bit positions are equal, then the chemical unit has the properties specified by the mask 114.

The techniques described above for generating the mask 114 and searching with a mask 114 also may be used to, perform searches with respect to sequences of chemical units or entire polymers. For example, if the search query 110 indicates a sequence of chemical units, the search engine 112 may fill the mask 114 with a sequence of bits corresponding to the concatenation of the binary encodings of the specified sequence of chemical units. The search engine 112 may then perform a binary AND operation on the polymer identifiers in the polymer database 102 using the mask 114, and generate the search results 116 as described above.

The techniques described above for generating the mask 114 and searching with the mask 114 are provided merely as an example. Other techniques for generating and searching with the mask 114 may also be used. The search engine 112 also may use more than one mask for each search query 110, and the search engine 112 may perform multiple binary operations in parallel in order to improve computational efficiency. In addition, binary operations other than a logical AND may be used to determine whether properties of the polymers in the polymer database 102 match the properties specified by the mask 114. Other binary operations include, for example, logical OR and logical XOR (exclusive or). Such binary operations may be used alone or in combination with each other.

Using the techniques described above, the polymer database 102 may be searched quickly for particular chemical units. One advantage of the process 300, if used in conjunction with a chemical unit coding scheme that encodes properties of chemical units using binary values is that a chemical unit identifier (e.g., the chemical unit identifier 204a) may be compared to a search query (in the form of a mask) using a single binary operation (e.g., a binary AND operation). As described above, conventional notation systems that use character-based notation systems to encode sequences of chemical units (e.g., systems which encode DNA sequences as sequences of characters) typically search for a sub-sequence of chemical units (represented by a first sequence of characters) within a super-sequence of chemical units (represented by a second sequence of characters) and use character-based comparison. Such a comparison typically is slow because it sequentially compares each character in a first sequence of characters (corresponding to the sub-sequence) to characters in a second sequence until a match is found. Consequently, the speed of the search is related to the length of the sub-sequence—i.e., the longer the sub-sequence, the slower the search.

In contrast, the speed of the techniques described above for searching binary operations may be constant in relation to the length of a sub-sequence that is the basis for the search query. Because the search engine 112 can search for a query sequence of chemical units using a single binary operation (e.g., a logical AND operation) regardless of the length of the query sequence, searches may be performed more quickly than conventional character-based methods whose speed is related to the length of the query sequence. Further, the binary operations used by the search engine 112 may be performed more quickly because conventional computer processors are designed to perform binary operations on binary data.

A further advantage of the techniques described above for searching using binary operations is that encoding one or more properties of a polymer into the notational representation of the polymer enables the search engine 112 to quickly and directly search the polymer database 102 for particular properties of polymers. Because the properties of a polymer are encoded into the polymer's notational representation, the search engine 112 may determine whether the polymer has a specified property by determining whether the specified property is encoded in the polymer's notational representation. For example, as described above, the search engine 112 may determine whether the polymer has the specified property by performing a logical AND operation on the polymer's notational representation using the mask 114. This operation may be performed quickly by conventional computer processors and may be performed using only the polymer's notational representation and the mask, without reference to additional information about the properties of the polymer.

Some aspects of the techniques described herein for representing properties using binary notation may be useful for generating, searching and manipulating information about polysaccharides. Accordingly, complete building block of a polymer may be assigned a unique numeric identifier, which may be used to classify the complete building block. For example, each numeric identifier may represent a complete building block of a polysaccharide, including the exact chemical structure as defined by the basic building block of a polysaccharide and all of its substituents, charges etc. A basic building block refers to a basic ring structure such as iduronic acid or glucuronic acid but does not include substituents, charges etc. Such building block information may be generated and processed in a same or similar manner as described above with respect to "properties" of polymers.

A computer system that may implement the system 100 of FIG. 1 as a computer program typically may include a main unit connected to both an output device which displays information to a user and an input device which receives input from a user. The main unit generally includes a processor connected to a memory system via an interconnection mechanism. The input device and output device also may be connected to the processor and memory system via the interconnection mechanism.

One or more output devices may be connected to the computer system. Example output devices include a cathode ray tube (CRT) display, liquid crystal displays (LCD), printers, communication devices such as a modem, and audio output. One or more input devices also may be connected to the computer system. Example input devices include a keyboard, keypad, track ball, mouse, pen and tablet, communication device, and data input devices such as sensors. The subject matter disclosed herein is not limited to the particular input or output devices used in combination with the computer system or to those described herein.

The computer system may be a general purpose computer system which is programmable using a computer programming language, such as C++, Java, or other language, such as a scripting language or assembly language. The computer system also may include specially-programmed, special purpose hardware such as, for example, an Application-Specific Integrated Circuit (ASIC). In a general purpose computer system, the processor typically is a commercially-available processor, of which the series x86, Celeron, and Pentium processors, available from Intel, and similar devices from AMD and Cyrix, the 680X0 series microprocessors available from Motorola, the PowerPC microprocessor from IBM and the Alpha-series processors from Digital Equipment Corporation, are examples. Many other processors are available. Such a microprocessor executes a program called an operating system, of which Windows NT, Linux, UNIX, DOS, VMS and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages may be written.

A memory system typically includes a computer readable and writeable nonvolatile recording medium, of which a magnetic disk, a flash memory and tape are examples. The disk may be removable, such as a "floppy disk," or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element typically allows for faster access to the information by the processor than does the disk. The processor generally manipulates the data within the integrated circuit memory and then copies the data to the disk after processing is completed. A variety of mechanisms are known for managing data movement between the disk and the integrated circuit memory element, and the subject matter disclosed herein is not limited to such mechanisms. Further, the subject matter disclosed herein is not limited to a particular memory system.

The subject matter disclosed herein is not limited to a particular computer platform, particular processor, or particular high-level programming language. Additionally, the computer system may be a multiprocessor computer system or may include multiple computers connected over a computer network. It should be understood that each module (e.g. 110, 120) in FIG. 1 may be separate modules of a computer program, or may be separate computer programs. Such modules may be operable on separate computers. Data (e.g., 104, 106, 110, 114 and 116) may be stored in a memory system or transmitted between computer systems. The subject matter disclosed herein is not limited to any particular implementation using software or hardware or firmware, or any combination thereof. The various elements of the system, either individually or in combination, may be implemented as a computer program product tangibly embodied in a machine-readable storage device for execution by a computer processor. Various steps of the process may be performed by a computer processor executing a program tangibly embodied on a computer-readable medium to perform functions by operating on input and generating output. Computer programming languages suitable for implementing such a system include procedural programming languages, object-oriented programming languages, and combinations of the two.

Having now described a few embodiments, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention.

What is claimed is:

1. A method for determining whether monosaccharides or disaccharides of a query sequence match monosaccharides or disaccharides of a polysaccharide, wherein the query sequence is represented by a first data structure, tangibly embodied in a computer-readable medium, including an identifier that includes fields, each field for storing a value for the monosaccharides or disaccharides of the query sequence, and wherein the polysaccharide is represented by a second data structure, tangibly embodied in a computer-readable medium, including an identifier that includes fields, each field for storing a value for the monosaccharides or disaccharides of the polysaccharide, wherein one or more of the values of the second data structure correspond to the nature and degree of sulfation or acetylation of the monosaccharides or disaccharides of the polysaccharide that alone do not provide the identity of the monosaccharides or disaccharides, the method comprising acts of:

(A) a user providing input for the fields of the first data structure with an input device, wherein one or more of the values of the first data structure correspond to the nature and degree of sulfation or acetylation of the monosaccharides or disaccharides of the query sequence that alone do not provide the identity of the monosaccharides or disaccharides;

(B) generating masks with the values stored in the fields of the first data structure;

(C) performing binary operations on the values stored in the fields of the second data structure with the masks to generate results; and (D) determining whether the monosaccharides or disaccharides of the query sequence match the monosaccharides or disaccharides of the polysaccharide with the results;

wherein the polysaccharide comprises disaccharide repeat units comprising hexosamine and glucuronic or iduronic acid that are linked by α/β1→4 glycosidic linkages.

2. The method of claim 1, wherein each of the fields of the first and second data structures is a bit field.

3. The method of claim 1, wherein each of the fields of the first and second data structures is a non-character based field.

4. The method of claim 1, wherein each of the identifiers of the first and second data structures is represented as a numerical identifier.

5. The method of claim 4, wherein each of the identifiers of the first and second data structures is represented as a single digit hexadecimal number.

6. The method of claim 4, wherein each of the identifiers of the first and second data structures is represented as a decimal value.

7. The method of claim 6, wherein the decimal value can be reduced to a plurality of prime divisors.

8. The method of claim 1, wherein the monosaccharides or disaccharides of the polysaccharide are monosaccharides.

9. The method of claim 1, wherein the monosaccharides or disaccharides of the polysaccharide are disaccharides.

10. The method of claim 1, wherein the values corresponding to the monosaccharides or disaccharides of the polysaccharide correspond to one or more properties of the monosaccharides or disaccharides of the polysaccharide.

11. The method of claim 10, wherein the one or more properties comprise the identity of the monosaccharides or disaccharides of the polysaccharide.

12. The method of claim 10, wherein the one or more properties comprise the exact chemical structure as defined by the basic building block of the polysaccharide.

13. The method of claim 10, wherein the one or more properties comprise the charge of the monosaccharides or disaccharides of the polysaccharide.

14. The method of claim 10, wherein the one or more properties comprise the molecular weight of the monosaccharides or disaccharides of the polysaccharide.

15. The method of claim 10, wherein the one or more properties comprise the nature and degree of sulfation of the monosaccharides or disaccharides of the polysaccharide.

16. The method of claim 10, wherein the one or more properties comprise the nature and degree of acetylation of the monosaccharides or disaccharides of the polysaccharide.

17. The method of claim 10, wherein the one or more properties comprise the nature or identity of substituents of the monosaccharides or disaccharides of the polysaccharide.

18. The method of claim 10, wherein the act of determining includes an act of determining that one or more properties of the monosaccharides or disaccharides of the query sequence match the one or more properties of the monosaccharides or disaccharides of the polysaccharide when the at least one result has a non-zero value.

19. The method of claim 1, wherein the at least one binary operation includes at least one logical AND operation.

20. The method of claim 2, wherein the at least one binary operation includes acts of performing a logical AND operation on the values stored in the bit fields of the second data structure using each of the masks to generate intermediate results, and combining the intermediate results using at least one logical OR operation to generate the results.

21. A method for determining whether a disaccharide of a query sequence matches a disaccharide of a polysaccharide, wherein the query sequence is represented by a first data structure, tangibly embodied in a computer-readable medium, including an identifier that includes one or more fields, each field for storing a value for the query sequence, and wherein the polysaccharide is represented by a second data structure, tangibly embodied in a computer-readable medium, including an identifier that includes one or more fields, each field for storing a value for the polysaccharide, wherein the second data structure comprises one or more values that indicate whether the polysaccharide contains an iduronic or glucuronic acid, the method comprising acts of:

(A) a user providing input for the one or more fields of the first data structure with an input device;

(B) generating at least one mask with the value or values stored in the one or more fields of the first data structure;

(C) performing at least one binary operation on the value or values stored in the one or more fields of the second data structure using the at least one mask to generate at least one result; and (D) determining whether the disaccharide of the query sequence match the disaccharide of the polysaccharide with the at least one result;

wherein the polysaccharide comprises disaccharide repeat units comprising hexosamine and glucuronic or iduronic acid that are linked by α/β1→4 glycosidic linkages.

22. The method of claim 10, wherein the one or more properties comprise the presence or absence of iduronic or glucuronic acid.

23. The method of claim 21, wherein one or more of the values of the second data structure correspond to the nature and degree of sulfation or acetylation of the disaccharide of the polysaccharide.

* * * * *